(12) United States Patent
Huang et al.

(10) Patent No.: US 8,679,824 B2
(45) Date of Patent: Mar. 25, 2014

(54) FERMENTATION BROTH FORMULATIONS

(75) Inventors: Tom Tao Huang, Fremont, CA (US);
Aaron Kelley, Fremont, CA (US); John McLaughlin, San Jose, CA (US)

(73) Assignee: Danisco US Inc., Palo Alto, CA (US)

( * ) Notice: Subject to any disclaimer, the term of this patent is extended or adjusted under 35 U.S.C. 154(b) by 1 day.

(21) Appl. No.: 13/201,997

(22) PCT Filed: Feb. 19, 2010

(86) PCT No.: PCT/US2010/024768
§ 371 (c)(1),
(2), (4) Date: Sep. 22, 2011

(87) PCT Pub. No.: WO2010/096673
PCT Pub. Date: Aug. 26, 2010

(65) Prior Publication Data
US 2012/0015422 A1    Jan. 19, 2012

Related U.S. Application Data (60) Provisional application No. 61/154,235, filed on Feb. 20, 2009, provisional application No. 61/185,865, filed on Jun. 10, 2009, provisional application No. 61/304,219, filed on Feb. 12, 2010.

(51) Int. Cl.
*C12N 1/00* (2006.01)
*C12N 9/24* (2006.01)
*C12N 9/42* (2006.01)
*A01N 37/10* (2006.01)

(52) U.S. Cl.
USPC ......... 435/254.1; 435/200; 435/209; 514/568

(58) Field of Classification Search
USPC .................. 435/254.1, 209, 200; 514/568
See application file for complete search history.

(56) References Cited

U.S. PATENT DOCUMENTS

| | | | |
|---|---|---|---|
| 5,378,621 A * | 1/1995 | Lawlis et al. ................. 435/183 |
| 5,789,210 A | 8/1998 | Ho | |
| 5,801,034 A * | 9/1998 | Lawlis et al. ................. 435/183 |
| 6,022,725 A | 2/2000 | Fowler | |
| 6,509,171 B1 | 1/2003 | Berka | |
| 6,982,159 B2 | 1/2006 | Dunn-Colemman | |
| 7,005,289 B2 | 2/2006 | Dunn-Colemman | |
| 7,045,332 B2 | 5/2006 | Dunn-Colemman | |
| 7,407,788 B2 | 8/2008 | Dunn-Colemman | |
| 7,582,462 B2 | 9/2009 | Dunn-Colemman | |

FOREIGN PATENT DOCUMENTS

| | | |
|---|---|---|
| EP | 0414404 A1 | 2/1991 |
| EP | 1133926 A1 | 9/2001 |
| WO | WO 90/15861 A1 | 12/1990 |
| WO | WO 01/67886 A1 | 9/2001 |
| WO | WO 02/95014 A2 | 5/2004 |
| WO | WO 2005/001036 A2 | 1/2005 |
| WO | WO 2007/118838 A1 | 10/2007 |
| WO | WO 2008/000714 A1 | 1/2008 |
| WO | WO 2008/113799 A1 | 9/2008 |

OTHER PUBLICATIONS

Berka et al, "Molecular Cloning and Deletion of the Gene Encoding Aspergifiopepsin A from *Aspergillus awamori*," *Gene*, 1990, 86:153-162.
Chen, H., et al., "Purification and Characterization of Two Extracellular β-glucosidases from *Trichoderma reesei*," *Biochimica et Biophysica Acta*, 1992, 1121, 54-60.
Ghose, T. K., "Measurement of Cellulase Activities," *Pure & Appl. Chem.*, 1987, 59, pp. 257-268.
Iwashita, et al., "The bglA Gene of *Aspergillus kawachii* Encodes Both Extracellular and Cell Wall-Bound β-Glucosidases," 1999, Appl. Environ. Microbiol. 65: 5546-5553.
Kawaguchi, et al., "Cloning and Sequencing of the cDNA Encoding P-glucosidase 1 from *Aspergillus aculeatus*," *Gene*, 1996 173: 287-288.
Machida, et al., "Nucleotide Sequences *Saccharomycopsis fibuligera* Genes for Extracellular β-Glucosidases as Expressed in *Saccharomyces cerevisiae*," *Appl. Environ. Microbiol.*, 1988, 54: 3147-3155.
Miller, "Use of Dinitrosalicylic Acid Reagent for Determination of Reducing Sugar," *Anal Chem.*, 1959, 31:426-428.
Schell, et al., "A Bioethanol Process Development Unit: Initial Operating Experiences and Results with a Corn Fiber Feedstock," *Bioresource Technology*, 2004, 91, 179-188.
Wood, et al., "The Genome Sequence of *Schizosaccharomyces pombe*," *Nature*, 2002, 415: 871-880.
Wong, et al., "The Cloning, Expression and Characterization of a Cellobiase Gene Encoding a Secretory Enzyme from *Cellulomonas Biazotea*," Gene, 1998, 207: 79-86.

\* cited by examiner

*Primary Examiner* — Chih-Min Kam
(74) *Attorney, Agent, or Firm* — Danisco US Inc.

(57) ABSTRACT

The present disclosure relates to fermentation broth formulations containing organic acids and/or organic acid salts, and methods of making and using such formulations.

71 Claims, 4 Drawing Sheets

FERMENTATION BROTH FORMULATIONS

CROSS-REFERENCE TO RELATED APPLICATIONS

This application is the National Stage of PCT Application No. PCT/US2010/024768, filed on Feb. 19, 2010, which claims the benefit of US Provisional Applications Ser. Nos. 61/154,235, filed Feb. 20, 2009, 61/185,865 filed on Jun. 10, 2009, and 61/304,219 filed Feb. 12, 2010, all of which are incorporated herein in their entirety.

1. FIELD OF THE INVENTION

The invention relates to fermentation broth formulations and methods of manufacturing and use thereof.

2. BACKGROUND

In various processes of culturing or fermenting microorganisms, it is sometimes necessary during or at the conclusion of the fermentation process to kill active cells in the mixture. This is particularly true when microorganisms containing recombinant DNA are grown as production hosts and it is desirable to prevent any viable recombinant organisms from being released into the environment. Even if the microorganisms do not contain recombinant DNA, it is often desirable to kill the cells prior to processing in order to ensure that viable cells are not released to the environment either in the product or in the waste products of the process.

Many conventional methods required to kill microorganisms, such as heat, are too severe and may destroy or alter the desired secreted product before the cells are killed. In this case, the product must be recovered without killing the cells, which requires the use of tedious and costly containment procedures and equipment. U.S. Pat. Nos. 5,801,034 and 5,378,621 describe a method for killing microbial cells with a single organic acid having 1 to 5 carbon atoms. However, according to the examples of these patents, a high level of organic acid and a low pH is optimal. The low pH condition is often detrimental to the stability of many enzyme products of interest in the fermentation medium and the high level of organic acid is often inhibitory to downstream applications in which it is desirable to use the enzyme products, such as fermentation of a microorganism that produces an organic substance on a substrate that has been produced by enzymatic catalysis with the enzyme product. Further, use of a high concentration of chemical agent for killing microbial cells may add significantly to the cost of the product recovered from the fermentation medium. Accordingly, there remains a need to develop methods of killing cells under less harsh conditions and with a lower concentration of chemical agents would be desirable.

3. BRIEF SUMMARY OF THE INVENTION

Many industrial proteins, such as enzymes, are often supplied commercially in the fermentation broths in which they are produced. Typically, the proteins are expressed and secreted by cells (recombinant or non-recombinant) into a fermentation broth containing a fermentation medium and the cells. It is often desirable to inactivate, e.g., kill, the cells prior to using the proteins in industrial applications so as not to release replicating cells into the environment. The present disclosure addresses the need to inactivate the cells in a manner that does not substantially interfere with the activity of the proteins, e.g., enzymes.

In certain aspects, the present disclosure provides a method of making a fermentation broth formulation, comprising incubating a first mixture comprising: (a) one or more fermentation broths, (b) a first organic acid component comprising at least one 1-5 carbon organic acid (i.e., an organic acid with a total of 1-5 carbons in its backbone and side chains) and/or a salt thereof in an amount of from 0.1% to 15% by weight of the first mixture, and (c) a second organic acid component comprising at least one 6 or more carbon organic acid (i.e., an organic acid with a total of 6 or more carbons in its backbone and side chains) and/or a salt thereof in an amount of from 0.025% to 5% by weight of the first mixture, for a time period and under conditions that result in at least a 4 log decrease in viable cells in said one or more fermentation broths, thereby making fermentation broth formulation.

In specific embodiments, the first organic acid component is in a range in which the lower limit is selected from 0.1%, 0.2%, 0.25%, 0.3%, 0.35%, 0.4%, 0.5%, 0.75%, or 1%, and in which the upper limit is independently selected from 0.3%, 0.4%, 0.5%, 0.75%, 1%, 2%, 3%, 5%, 7%, 10%, 12%, or 15% by weight of the first mixture, for example in amounts ranging from 0.2% to 1%, from 0.2% to 0.5%, from 0.1% to 10%, from 0.25% to 5% or from 0.3% to 3% by weight of the first mixture, etc.

In specific embodiments, the second organic acid component is in a range in which the lower limit is selected from 0.025%, 0.03%, 0.04%, 0.045%, 0.05%, 0.075%, 0.1%, 0.2%, 0.25%, 0.3%, 0.35%, 0.4%, 0.5%, 0.75%, or 1%, and in which the upper limit is independently selected from 0.1%, 0.2%, 0.3%, 0.4%, 0.5%, 0.75%, 1%, 2%, 3%, or 5% by weight of the first mixture, for example in amounts ranging from 0.04% to 3%, from 0.2% to 0.5%, from 0.1% to 1%, from 0.25% to 5% or from 0.3% to 3% by weight of the first mixture, etc. The organic acid can suitably be a 6- to 10-carbon organic acid, a 6- to 9-carbon organic acid, or a 6- to 8-carbon organic acid. Thus, in specific embodiments, the second organic acid component comprises or consists of a 6-carbon acid and/or a salt thereof, a 7-carbon acid and/or a salt thereof, an 8-carbon acid and/or a salt thereof, a 9-carbon acid and/or a salt thereof, or a 10-carbon acid acid and/or a salt thereof.

The time period for the incubation is suitably in a range in which the lower limit is selected from 4 hours, 6 hours, 8 hours, 10 hours, 12 hours, 14 hours, 16 hours, 18 hours or 20 hours, and in which the upper limit is independently selected from 12 hours, 16 hours, 20 hours, 24 hours, 28 hours, 32 hours or 36 hours, for example from 4 hours to 36 hours, for example from 8 hours to 36 hours, from 20 hours to 28 hours, from 8 hours to 16 hours, from 10 hours to 20 hours, from 16 hours to 30 hours, etc.

The conditions for the incubation include a temperature that is suitably in a range in which the lower limit is selected from 20° C., 22° C., 25° C., 28° C., 30° C., 32° C., 34° C., 36° C., 38° C., or 40° C., and in which the upper limit is independently selected from 28° C., 33° C., 35° C., 40° C., 45° C., 50° C., or 55° C., for example from 20° C. to 50° C., from 25° C. to 40° C., from 28° C. to 33° C., etc.

The conditions for the incubation include a pH that is suitably in a range in which the lower limit is selected from 3.5, 3.6, 3.7, 3.8, 3.9, 4, or 4.2, and in which the upper limit is independently selected from 3.8, 4, 4.2, 4.4, 4.5, 4.6, 4.7, 4.8, 4.9, 5, 5.2, or 5.5, for example a pH from 3.5 to 5, from 4 to 4.7, or 4.2 to 4.5. The pH can be adjusted at the onset of the incubation and/or one or more times during the incubation period, for example adding a pH-adjusting agent. In specific embodiments, the pH-adjusting agent is phosphoric acid, sulfuric acid or sodium hydroxide. It is also contemplated herein that in certain embodiments the first and/or second organic acid component can play a role in adjusting the pH at the onset of the incubation and/or during the incubation period, and thus partly or wholly alleviate the need for further pH adjusting agents.

In certain aspects, the methods of the disclosure accomplish at least a 5 log decrease, a 6 log decrease, a 7 log decrease or an 8 log decrease in the number of viable cells in one or more fermentation broths in the mixture.

In specific embodiments, the decrease in viable cells in said at least 0.25-fold, at least 0.5-fold, at least 1-fold, at least 2-fold, at least 5-fold or at least 10-fold greater than for a second mixture or alternative mixture subjected to said conditions that contains only one organic acid component in an amount of up to the total weight percentages of the first and second organic acid components in the first mixture. By way of example, the use of a first amount (e.g., 1% by weight) of a first organic acid component and a second amount (0.5% percent by weight) of a second organic acid component in connection with the methods of the disclosure results in a greater decrease of number of viable cells than the use of a third amount that is up to the sum of said first and second amounts (e.g., 1.5% weigh percent) of the first organic acid component or second organic acid component alone under the same or similar conditions.

The present methods can be used to inactivate fungal cells, for example filamentous fungal cells. In specific embodiments, the filamentous fungal cells are from the genera *Trichoderma, Aspergillus, Penicillium, Humicola, Chrysosporium,* or *Neurospora*. Further cell type suitable for the methods, formulations and compositions of the present disclosure are described in Section 5.2.1, infra.

In specific embodiments, first organic acid component comprises or consists of acetic acid, a salt of acetic acid, formic acid, a salt of formic acid, propionic acid, a salt of propionic acid, or a mixture of two or more of the foregoing. In one embodiment, the first organic acid component comprises or consists of acetic acid and/or a salt thereof.

In specific embodiments, the second organic acid component comprises or consists of benzoic acid, a salt of benzoic acid, cyclohexanecarboxylic acid, a salt of cyclohexanecarboxylic acid, 4-methylvaleric acid, a salt of 4-methylvaleric acid, phenylacetic acid, a salt of phenylacetic acid, or a mixture of two or more of the foregoing. In one embodiment, the second organic acid component comprises or consists of benzoic acid and/or a salt thereof.

In certain embodiments of the present methods, the first organic acid component comprises a sodium, potassium, calcium or magnesium salt of said 1-5 carbon organic acid and/or the second organic acid component comprises a sodium, potassium, calcium or magnesium salt of said 6 or more carbon organic acid.

In certain specific embodiments, the first organic acid component comprises acetic acid at a concentration of 0.2%-0.4% by weight and the second organic acid component comprises sodium benzoate at a concentration of 0.2%-0.4% by weight and/or the time period is 24 hours and/or the conditions include temperature of 40° C. and/or the conditions include a pH of between 4 and 4.6.

In the methods of the disclosure, the first mixture can also contain one or more anti-microbial agents, for example to inhibit the growth of contaminating bacteria or fungi. In specific embodiments, the one or more anti-microbial agents are in an amount of 0.0005 to 0.05 percent by weight of the first mixture, for example in an amount of 0.001 to 0.025 percent by weight of said the mixture. In a specific embodiment, the antimicrobial agent comprises hops extract containing iso-alpha-acids, tetra-iso alpha acids, and/or beta acids. It is also contemplated herein that in certain embodiments the first and/or second organic acid component can play an anti-microbial role, and thus partly or wholly alleviate the need for further anti-microbial agents.

The present methods can further comprise the step of making the first mixture prior to the incubating step described above, for example by combining one or more fermentation broths with at least one 1-5 carbon organic acid and/or a salt thereof, at least one 6 or more carbon organic acid and/or a salt thereof and optionally one or more further reagents, such as a pH adjusting agent and/or an anti-microbial agent.

In certain embodiments, the methods described herein further comprise a step of culturing cells to produce one or more of the fermentation broths employed in the present disclosure. By way of example but not limitation, the fermentation broths can be prepared according to any of the cell culture methods described in Section 5.2.2, infra. Accordingly, the compositions and formulations of the present disclosure can include fermentation broths prepared by the methods disclosed herein.

Without being bound by any theory, the present inventors believe that the use of the two organic acid components described herein results in reducing the overall organic acid component required to achieve cell inactivation (e.g., by reducing the number of viable cells by a 4 or more log factor as described herein) as compared to using a single organic acid component and allows the incubation reaction to be carried out at a greater pH than otherwise possible, thereby minimizing adverse effects on folding and stability of proteins, e.g., enzymes, in the starting fermentation broth. Thus, in certain aspects, the present methods are carried out under conditions that result in a fermentation broth formulation in which one or more enzymes retain at least 75%, at least 80%, at least 85%, at least 90%, at least 95% or at least 98% of their starting enzymatic activity.

The present disclosure further provides a fermentation broth formulation obtained or obtainable by the methods described herein.

Thus, in certain aspects, the present disclosure provides a composition comprising (a) one or more fermentation broths comprising cells; (b) a first organic acid component comprising at least one 1-5 carbon organic acid and/or a salt thereof in an amount of 0.2% to 1.5% by weight of said composition, (c) a second organic acid component comprising at least one 6 or more carbon organic acid and/or a salt thereof in an amount of 0.04% to 0.6% by weight of said composition.

In specific embodiments, the first organic acid component is in a range in which the lower limit is selected from 0.1%, 0.2%, 0.25%, 0.3%, 0.35%, 0.4%, 0.5%, 0.75%, or 1%, and in which the upper limit is independently selected from 0.3%, 0.4%, 0.5%, 0.75%, 1%, 2%, 3%, 5%, 7%, 10%, 12%, or 15% by weight of the composition, for example in amounts ranging from 0.2% to 1%, from 0.2% to 0.5%, from 0.1% to 10%, from 0.25% to 5% or from 0.3% to 3% by weight of the composition, etc.

In specific embodiments, the second organic acid component is in a range in which the lower limit is selected from 0.025%, 0.03%, 0.04%, 0.045%, 0.05%, 0.075%, 0.1%, 0.2%, 0.25%, 0.3%, 0.35%, 0.4%, 0.5%, 0.75%, or 1%, and in which the upper limit is independently selected from 0.1%, 0.2%, 0.3%, 0.4%, 0.5%, 0.75%, 1%, 2%, 3%, or 5% by weight of the composition, for example in amounts ranging from 0.04% to 3%, from 0.2% to 0.5%, from 0.1% to 1%, from 0.25% to 5% or from 0.3% to 3% by weight of the composition, etc.

It is to be understood that the organic acid components in the formulations and compositions of the disclosure are typically at least partly in dissociated form and, when such components are in dissociated form, the weight percent of the component refers not to the weight of the dissociated ions (e.g., cation) but to the weight of the dry material (e.g., acid or salt) used in making the composition or formulation. The degree to which such components are dissociated will depend on their respective pKa values. It is preferred that formulation or composition is made under pH conditions and temperature in which at least 20%, at least 30%, at least 40%, at least 50%, at least 60% or at least 70% of the organic acid component is dissociated.

In certain aspects, the composition of the disclosure are at a pH that is suitably in a range in which the lower limit is selected from 3.5, 3.6, 3.7, 3.8, 3.9, 4, or 4.2, and in which the upper limit is independently selected from 3.8, 4, 4.2, 4.4, 4.5, 4.6, 4.7, 4.8, 4.9, 5, 5.2, or 5.5, for example a pH from 3.5 to 5, from 4 to 4.7, or 4.2 to 4.5.

In certain aspects, the cells in a composition of the disclosure are predominantly or completely nonviable cells. For example, in certain embodiments, if viable cells are present in the composition, then the ratio of nonviable cells to viable cells in said composition is at least 10:1, at least 50:1, at least 100:1, at least 1000:1, at least 10,000:1, at least 100,000:1 or at least 1,000,000:1.

In certain aspects, the cells comprise fungal cells, for example filamentous fungal cells. In specific embodiments, the filamentous fungal cells are from the genera *Trichoderma, Aspergillus, Penicillium, Humicola, Chrysosporium,* or *Neurospora*.

In certain embodiments of the compositions of the disclosure, the first organic acid component comprises or consists of acetic acid, a salt of acetic acid, formic acid, a salt of formic acid, propionic acid, a salt of propionic acid, or a mixture of two or more of the foregoing. In a specific embodiment, the first organic acid component comprises or consists of acetic acid and/or a salt thereof.

In certain embodiments of the composition of the disclosure, the second organic acid component comprises or consists of benzoic acid, a salt of benzoic acid, cyclohexanecarboxylic acid, a salt of cyclohexanecarboxylic acid, 4-methylvaleric acid, a salt of 4-methylvaleric acid, phenylacetic acid, a salt of phenylacetic acid, or a mixture of two or more of the foregoing. In a specific embodiment, the second organic component comprises or consists of benzoic acid and/or a salt thereof.

In certain embodiments, the first organic acid component comprises a sodium, potassium, calcium or magnesium salt of a 1-5 carbon organic acid and/or the second organic acid component comprises a sodium, potassium, calcium or magnesium salt of a 6 or more carbon organic acid.

Further details and embodiments of the organic acids suitable in the methods and compositions of the present disclosure are described in Section 5.2.4, infra.

In specific embodiments, the first organic acid component comprises acetic acid at a concentration of 0.2%-0.4% by weight and/or the second organic acid component comprises sodium benzoate at a concentration of 0.2%-0.4% by weight.

The compositions of the disclosure can comprise one or more anti-microbial agents. In specific embodiments, the one or more anti-microbial agents are in an amount of 0.0005 to 0.05 percent by weight of the composition, for example in an amount of 0.001 to 0.025 percent by weight of said composition. In a specific embodiment, the antimicrobial agent comprises hops extract containing iso-alpha-acids, tetra-iso alpha acids, and/or beta acids.

The fermentation broths used in the methods, formulations and compositions of the disclosure typically contain at one or more proteins secreted by the cells. At least one of said one or more proteins can be expressed recombinantly and/or is an enzyme, for example an exoglucanase, an endoglucanase, a hemicellulase or a β-glucosidase. In certain embodiments, the fermentation broths contain a plurality of enzymes expressed recombinantly and secreted by the cells, for example two or more of an exoglucanase, an endoglucanase, a hemicellulase or a β-glucosidase. Further enzymes that are suitably present in the compositions and formulations of the present disclosure are described in Section 5.2.3, infra. In certain aspects, proteins constitute from 3 to 30 weight percent of a formulation or composition of the disclosure. In specific embodiments, proteins constitute 5 to 15 weight percent, from 7 to 10 weight percent, from 6 to 12 weight percent, from 5 to 20 weigh percent, from 10 to 25 weight percent, from 10 to 20 weight percent, from 8 to 15 weight percent from or from 6 to 10 weight percent of the formulation or composition of the disclosure.

In certain specific embodiments a formulation or composition of the disclosure has one, two, or all three of the following activities:

(a) an endoglucanase activity ranging from a lower limit that is selected from 2000, 2100, 2200, 2350, 2500 or 2650 CMC U/g to an upper limit that is independently selected from 2400, 2600, 2800, 3000, 3200, 3500, 3750 or 4000 CMC U/g, for example in a range of from 2200 CMC U/g to 2800 CMC U/g, from 2200 CMC U/g to 3200 CMC U/g, from 2500 to 3500 CMC U/g, etc.;

(b) a β-glucosidase activity ranging from a lower limit that is selected from 300, 375, 450, 475, 500, 525, 550, 600, 650, or 700 pNPG U/g to an upper limit that is independently selected from 475, 525, 575, 635, 700, 775, 800, 850, 900 or 950 pNPG U/g, for example in a range of from 525 pNPG U/g to 775 pNPG U/g, from 300 pNPG U/g to 800 pNPG U/g, from 350 pNPG U/g to 850 pNPG U/g, etc.; and (c) a xylanase activity ranging from a lower limit that is selected from 1000, 1250, 1500, 1750, 2000, 2250, 2500, 2750 or 3000 ABX U/g to an upper limit that is independently selected from 2500, 3000, 3500, 4000, 4500, 5000, 5500, 6000 or 7000 ABX U/g, for example in a range of from 2000 ABX U/g to 5000 ABX U/g, from 1500 ABX U/g to 4500, ABX U/g, from 3500 ABX U/g to 5500 ABX U/g, etc.

In another aspect, the invention provides a method of hydrolyzing a cellulosic material, comprising contacting the cellulosic material with any of the foregoing fermentation broth formulations or compositions. In some embodiments, the cellulosic material is a plant biomass material, such as a lignocellulosic material which optionally has been pretreated to enhance enzymatic hydrolysis. Accordingly, in certain aspects the formulations and compositions of the disclosure further comprise an unhydrolyzed cellulosic material, partially hydrolyzed cellulosic material, or substantially wholly hydrolyzed (e.g., >90% hydrolyzed or >95% hydrolyzed) cellulosic material. In specific embodiments, the partially hydrolyzed cellulosic material (i) is up to 40%, up to 50%, up 60%, up to 70%, up to 80% or up to 90% hydrolyzed cellulosic material; (ii) is at least 30%, at least 40%, at least 50%, at least 60%, or at least 70% hydrolyzed cellulosic material; or (iii) is hydrolyzed to a range falling between an pair of the values selected independently from (i) and (ii), e.g., 30%-80% or 40%-90% hydrolyzed. It is noted that the weight ranges of the components (e.g., organic acids) of the formulations and compositions described herein generally do not include cellulosic materials or products of hydrolysis of cellulosic materials.

Further details and embodiments of the formulations and compositions of the present disclosure are described in Section 5.3, infra.

In aspects, the disclosure provides methods of producing organic substances by fermenting a microorganism that produces an organic substance in a formulation or composition of the disclosure. In one embodiment, the microorganism is an ethanologenic microorganism and the organic substance is ethanol. A composition of the disclosure can be used in a simultaneous saccharification and fermentation reaction ("SSF") or a separate hydrolysis and fermentation reaction ("SHF").

Without being bound by any theory, the formulations and compositions of the disclosure advantageously contain fewer inhibitors of fermenting microorganisms than a formulation or composition (referred to herein as an "alternative formulation" or "alternative composition," respectively) that is similar or identical to a composition of the disclosure but containing only one organic acid component in an amount to inactivate or kill the cells in the fermentation broth(s) in the alternative formulation or composition. Accordingly, in certain embodiments, the yield of organic substance in the produced by the fermenting microorganism in the presence of the formulation or composition of the disclosure is at least 0.25-fold greater, at least 0.5-fold greater, at least 1-fold greater, at least 2-fold greater, at least 5-fold greater or at least 10-fold greater than the yield of organic substance in the presence of such an alternative formulation or composition. By way of example, when a composition or formulation of the disclosure containing enzymes, a first amount (e.g., 1% by weight) of a first organic acid component and a second amount (0.5% percent by weight) of a second organic acid component is employed with a fermenting microorganism, the yield of organic substance produced by the fermenting microorganism is greater than the yield when a composition containing the same enzymes and a third amount that is up to the sum of said first and second amounts (e.g., 1.5% weigh percent) of the first organic acid component or second organic acid component alone is employed under the same or similar conditions.

Thus, in certain embodiments, the present formulations and compositions are used in an SSF reaction. The methods comprise subjecting a SSF reaction mixture containing a formulation or composition of the disclosure, a fermenting microorganism and a cellulosic substrate to SSF conditions. Optionally, the methods include the step of forming the SSF reaction mixture, for example by combining a formulation or composition of the disclosure, the ethanologen and, optionally the cellulosic substrate. In a specific embodiment, the SSF conditions include the absence of a supplemental nitrogen source. In another specific embodiment, the conditions are conducive both to hydrolysis of cellulose to glucose and/or hemi-cellulose sugar (e.g., xylose, arabinose, and/or mannose) and to conversion of glucose and/or hemi-cellulose to the organic substance (e.g., ethanol). SSF reaction mixtures comprising a formulation or composition of the disclosure, a fermenting microorganism, and, optionally, a cellulosic material are also encompassed by the present disclosure, are as SSF reaction products in which the cellulosic material has been at least partially hydrolyzed and fermented.

In other embodiments, the present formulations and compositions are used in a SHF reaction. The methods comprise subjecting a SHF reaction mixture containing a formulation or composition of the disclosure and a cellulosic substrate to SHF conditions. Optionally, the methods include the step of forming the SHF reaction mixture, for example by combining a formulation or composition of the disclosure and a cellulosic substrate. In a specific embodiment, the SHF conditions are conducive to hydrolysis of cellulose to glucose and/or hemi-cellulose sugar (e.g., xylose, arabinose, and/or mannose). Optionally, the SHF reaction products are then used in a fermentation reaction for conversion of the resulting glucose and/or hemi-cellulose to the organic substance (e.g., ethanol). SHF reaction mixtures comprising a formulation or composition of the disclosure and a cellulosic material are also encompassed by the present disclosure, as are SHF reaction products in which the cellulosic material has been at least partially hydrolyzed.

Further details and embodiments of methods for hydrolyzing cellulosic material and methods of producing organic substances are described in Sections 5.4 and 5.5, infra.

In another aspect, the invention provides kits containing packaging and a formulation, composition, SSF reaction mixture, SSF reaction product, SHF reaction mixture or SHF reaction product according to the present disclosure. In some embodiments, the kit further contains instructions for use in a method for producing an organic substance with a fermenting microorganism, for example, instructions for use in a method for producing ethanol with an ethanologenic microorganism and a cellulosic substrate hydrolyzed with the cell-killed whole broth or composition in the kit. Further details and embodiments of the kits of the present disclosure are described in Section 5.6, infra.

Further specific embodiments of the methods, formulations and compositions of the present disclosure are provided in Section 5.7, infra.

5. DETAILED DESCRIPTION

5.1 Definitions

As used herein, the term "host cell" refers to a cell or cell line into which a recombinant expression vector for production of a polypeptide may be transfected for expression of the polypeptide. Host cells include progeny of a single host cell, and the progeny may not necessarily be completely identical (in morphology or in total genomic DNA complement) to the original parent cell due to natural, accidental, or deliberate mutation. A host cell includes cells transfected or transformed in vivo with an expression vector. "Host cell" refers to both cells and protoplasts created from the cells of a filamentous fungal strain and particularly a *Trichoderma* sp. strain.

The term "recombinant" when used in reference to a cell, nucleic acid, protein or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

"Filamentous fungi" refers to all filamentous forms of the subdivision *Eumycotina* and *Oomycota* (See, Alexopoulos, C. J. (1962), *Introductory Mycology*, Wiley, New York). These fungi are characterized by a vegetative mycelium with a cell wall composed of chitin, beta-glucan, and other complex polysaccharides. The filamentous fungi of the present invention are morphologically, physiologically, and genetically distinct from yeasts. Vegetative growth by filamentous fungi is by hyphal elongation and carbon catabolism is obligatorily aerobic.

As used herein, the term "*Trichoderma*" or "*Trichoderma* sp.*" refers to any fungal genus previously or currently classified as *Trichoderma*.

The term "culturing" refers to growing a population of microbial cells under suitable conditions for growth, in a liquid or solid medium.

As used herein, the terms "cellulosic substrate" or "cellulosic material," used interchangeably herein, refer to a material containing cellulose and/or hemi-cellulose. A cellulosic substrate may be a lignocellulosic material, which contains cellulose, hemi-cellulose, and beta-glucans that are cross-linked with each other and with lignin. Such cellulosic substrates may also contain other materials, such as pectins, proteins, starch, and lipids, but typically contain cellulose, hemi-cellulose, and beta-glucans as primary components.

A "fermenting microorganism" refers to any microorganism suitable for use in a desired fermentation process for the production of organic substances.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or non-viable microbial cells.

"Ethanologenic" refers to the ability of a microorganism to produce ethanol from a carbohydrate as a primary fermentation product. In some embodiments, ethanologenic microorganisms may also be used to produce other organic substances.

A "carboxymethylcellulose unit" or "CMC U" refers to a unit of endoglucanase activity that liberates 1 µmol of reducing sugar (expressed as glucose equivalents) in one minute at 50° C. and pH 4.8.

A "pNP-glucoside unit" or "pNPG U" refers to a unit of beta-glucosidase activity that liberates 1 µmol of nitrophenol from para-nitrophenyl-B-D-glucopyranoside at 50° C. and pH 4.8.

A "ABX unit" or "ABX U" refers to a unit of xylanase activity that liberates 1 mmol xylose reducing sugar equivalents from a solution of 1% xylan from birchwood in 50 mM citric-Na citrate buffer pH 5.3 at 50° C., as assayed using the dinitrosalicylic acid (DNS) method (Miller, 1959, Anal Chem., 31:426-428).

5.2 Methods of Killing Cells

The invention provides methods for killing cells in a culture medium, thereby producing a cell-killed whole broth. In some embodiments, the method includes contacting the cells with a combination of a first organic acid having 1 to 5 carbon atoms, at a concentration of about 0.2% to about 1% by weight, and a second organic acid having 6 or more carbon atoms, at a concentration of about 0.04% to about a 0.3% by weight. In some embodiments, the method includes contacting the cells with a combination of a first organic acid having 1 to 5 carbon atoms, at a concentration of about 0.2% to about 0.5% by weight, and a second organic acid having 6 or more carbon atoms, at a concentration of about 0.2% to about 0.5% by weight. In other embodiments, the method includes contacting the cells with an organic acid having 6 or more carbon atoms at a concentration of about 0.25% to about 0.5% by weight. The method is performed for a suitable period of time and at a suitable pH and temperature to effect substantially complete (i.e., at least about 4, 5, or 6 log decrease in viable cells after treatment) or complete (i.e., no viable cells after treatment) cell kill. Typically, the pH is about 3.5 to about 4.5, about 4 to about 4.4, or about 3.9 to about 4.2, the temperature is about 30° C. to about 40° C., and the method is performed at this pH and temperature for about 8 to about 24 hours. In one embodiment, the method is performed at pH about 4 and temperature about 40° C. for about 24 hours. In some embodiments, the cells are killed without lysis. In some embodiments, some or all of the cells are lysed.

5.2.1 Microbial Cells

The cells are typically microbial cells, for example, bacterial or fungal cells, and typically produce at least one molecule of interest, such as an enzyme or organic compound. In some embodiments, the cells produce at least one enzyme that is expressed recombinantly. In some embodiments, the molecule of interest is secreted into the extracellular culture medium. In some embodiments, the molecule of interest is produced intracellularly and is not secreted extracellularly into the culture medium. When the molecule is produced intracellularly and not secreted extracellularly, lysis of the killed cells may be required to release the molecule into the liquid medium.

In some embodiments, the microbial cells are filamentous fungal cells, including naturally occurring filamentous fungi, filamentous fungi with naturally occurring or induced mutations, and filamentous fungi that have been genetically modified.

In some embodiments, the fungal cells are *Aspergillus, Acremonium, Aureobasidium, Beauveria, Bjerkandera, Cephalosporium, Ceriporiopsis, Chaetomium, Chrysosporium, Claviceps, Cochiobolus, Coprinus, Coriolus, Corynascus, Cryptococcus, Cyathus, Endothia, Endothia, Filobasidium, Fusarium, Gilocladium, Humicola, Magnaporthe, Myceliophthora, Myrothecium, Mucor, Neocallimastix, Neurospora, Paeilomyces, Penicillium, Phanerochaete, Phlebia, Piromyces, Pleurotus, Podospora, Paecilomyces, Pyricularia, Rhizomucor, Rhizopus, Schizophylum, Sporotrychum, Stagonospora, Talaromyces, Toypoladium, Trichoderma, Thermomyces, Thermoascus, Thielavia, Tolypocladium, Trichophyton,* and *Trametes* species or species derived therefrom. In some embodiments, the fungal cells are *Aspergillus aculeatus, Aspergillus awamori, Aspergillus foetidus, Aspergillus japonicus, Aspergillus nidulans, Aspergillus niger, Aspergillus fumigatus,* or *Aspergillus oryzae*. In some embodiments, the fungal cells are *Fusarium bactridioides,*

*Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides*, or *Fusarium venenatum*. In some embodiments, the fungal cells are *Bjerkandera adusta, Ceriporiopsis aneirina, Ceriporiopsis caregiea, Ceriporiopsis gilvescens, Ceriporiopsis pannocinta, Cerporiopsis rivulosa, Ceriporiopsis subrufa, Ceriporiopsis subvermispora, Coriolus hirsutus, Humicola insolens, Humicola lanuginosa, Mucor miehei, Myceliophthora thermophila, Neurospora crassa, Scytalidium thermophilum, Thielavia terrestris, Trametes pleurotus, Trametes villosa, Trametes versicolor, Chaetomium paecilomyces, Endothia mucor, Penicillium purpurogenum, Penicillium funiculosum, Phanerochaete chrysosporium, Phlebia radiate,* or *Pleurotus eryngii*. In some embodiments, the fungal cells are *Trichoderma harzianum, Trichoderma koningii, Trichoderma longibrachiatum, Trichoderma reesei,* or *Trichoderma viride*.

5.2.2 Culturing of Microbial Cells

Microbial cells may be cultured by any cultivation method known in the art resulting in the expression. Generally, conditions suitable for production of one or more molecules of interest (e.g., one or more enzyme and/or organic compound) are used, for example, conditions suitable for expression of enzymes capable of hydrolyzing a cellulosic substrate. Fermentation of a microbial culture can include shake flask cultivation, small- or large-scale fermentation, such as continuous, batch, fed-batch, or solid state fermentations in laboratory or industrial fermenters performed in a suitable medium and under conditions allowing cellulase to be expressed. The cultivation takes place in a suitable nutrient medium comprising carbon and nitrogen sources and inorganic salts, using procedures known in the art. Suitable culture media, temperature ranges and other conditions suitable for growth and production of molecules of interest, e.g., biomolecules, such as enzymes or other proteins, or organic compounds, are known in the art.

Fermentation, e.g., fermentation of filamentous fungal cells, is often conducted in such a manner that the carbon-containing substrate can be controlled as a limiting factor, thereby providing good conversion of the carbon-containing substrate to cells and avoiding contamination of the cells with a substantial amount of unconverted substrate. The latter is not a problem with water-soluble substrates, since any remaining traces are readily washed off. It may be a problem, however, in the case of non-water-soluble substrates, and require added product-treatment steps such as suitable washing steps.

The fermentation can be conducted by growing the microbial cells, e.g., filamentous fungal cells, to stationary phase and maintaining cells under limiting carbon conditions for a period of time sufficient to express one or more molecule of interest.

5.2.3 Enzymes Expressed by Microbial Cells

Microbial cells used in the methods of the invention may be non-recombinant and/or recombinant, e.g., non-recombinant and/or recombinant filamentous fungi. In some embodiments the microbial cells contain one or more genes which can be homologous or heterologous to the microbial cells.

In some embodiments, the microbial cells, e.g, filamentous fungal cells, contain one or more genes which can be homologous or heterologous to the cells, wherein the one or more genes encode enzymes that can degrade a cellulosic substrate. Genes encoding cellulosic material degrading enzymes are known to those skilled in the art. Suitable non-limiting examples of genes that encode enzymes that degrade cellulosic substrates include endoglucanases, cellobiohydrolases, glucohydrolases, beta-glucosidases, xyloglucanases, xylanases, xylosidases, alpha-arabinofuranosidases, alpha-glucuronidases, acetyl xylan esterases, mannanases, mannosidases, alpha-galactosidases, mannan acetyl esterases, galactanases, arabinanases, pectate lyases, pectin lyases, pectate lyases, polygalacturonases, pectin acetyl esterases, pectin methyl esterases, alpha-arabinofuranosidases, beta-galactosidases, galactanases, arabinanases, alpha-arabinofuranosidases, rhamnogalacturonases, rhamnogalacturonan lyases, and rhamnogalacturonan acetyl esterases, xylogalacturonosidases, xylogalacturonases, rhamnogalacturonan lyases, lignin peroxidases, manganese-dependent peroxidases, and laccases.

In some embodiments of the invention, recombinant microbial cells, e.g., recombinant filamentous fungal cells, over-express an enzyme(s) to improve the degradation of the cellulosic substrate. Alternatively, the microbial cells may be a mixture of non-recombinant cells and recombinant cells over-expressing an enzyme(s) to improve the degradation of the cellulosic substrate. In some embodiments of the invention, the microbial cells, e.g., filamentous fungal cells, over-expressing β-glucosidase. Alternatively, the microbial cells may be a mixture of non-recombinant cells and recombinant cells over-expressing a β-glucosidase.

The term "beta-glucosidase" is defined herein as a beta-D-glucoside glucohydrolase classified as EC 3.2.1.21, and/or those in certain GH families, including, but not limited to, those in GH families 1, 3, 7, 9 or 48, which catalyze the hydrolysis of cellobiose with the release of beta-D-glucose. The over-expressed beta-glucosidase can be from the same or different species than that of the host cell. Notably, the over-expressed beta-glucosidase need not be a fungal beta-glucosidase to be expressed in a fungal cell.

In some embodiments, the beta-glucosidase can be produced by expressing a gene encoding beta-glucosidase. For example, beta-glucosidase can be secreted into the extracellular space, e.g., by Gram-positive organisms, (such as *Bacillus* and *Actinomycetes*), or eukaryotic hosts (e.g., *Trichoderma, Aspergillus, Saccharomyces,* and *Pichia*). It is to be understood, that in some embodiments, beta-glucosidase can be over-expressed in a recombinant microorganism relative to the native levels. In some embodiments, if a host cell is employed for expression of the beta-glucosidase, the cell may be genetically modified to reduce expression of one or more proteins that are endogenous to the cell. In one embodiment, the cell may contain one or more native genes, particularly genes that encode secreted proteins that have been deleted or inactivated. For example, one or more protease-encoding genes (e.g., an aspartyl protease-encoding gene; see Berka et al, Gene 1990 86:153-162 and U.S. Pat. No. 6,509,171) or cellulase-encoding genes may be deleted or inactivated. In one embodiment, a *Trichoderma* sp. host cell, e.g., a *T. reesei* host cell, contains inactivating deletions in the cbh1, cbh2 and egl1, and egl2 genes, as described in PCT Application No. WO05/001036. The nucleic acid encoding beta-glucosidase may be present in the nuclear genome of the *Trichoderma* sp. host cell or may be present in a plasmid that replicates in the *Trichoderma* host cell.

Examples of beta-glucosidase that can be used include beta-glucosidase from *Aspergillus aculeatus* (Kawaguchi et al., 1996, Gene 173: 287-288), *Aspergillus kawachi* (Iwashita et al., 1999, Appl. Environ. Microbiol. 65: 5546-5553), *Aspergillus oryzae* (WO2002/095014), *Cellulomonas biazotea* (Wong et al., 1998, Gene 207: 79-86), *Saccharomycopsis*

*fibuligera* (Machida et al., 1988, Appl. Environ. Microbiol. 54: 3147-3155), *Schizosaccharomyces pombe* (Wood et al., 2002, Nature 415: 871-880), *Trichoderma reesei* beta-glucosidase 1 (U.S. Pat. No. 6,022,725), *Trichoderma reesei* beta-glucosidase 3 (U.S. Pat. No. 6,982,159), *Trichoderma reesei* beta-glucosidase 4 (U.S. Pat. No. 7,045,332), *Trichoderma reesei* beta-glucosidase 5 (U.S. Pat. No. 7,005,289), *Trichoderma reesei* beta-glucosidase 6 (USPN 20060258554), and *Trichoderma reesei* beta-glucosidase 7 (USPN 20040102619).

In some embodiments, enzyme(s) of interest secreted extracellularly by the microbial cells are soluble in the extracellular culture medium and/or in the cell killed broth. In some embodiments, enzyme(s) of interest secreted extracellularly by the microbial cells are insoluble in the extracellular culture medium and/or in the cell killed broth. In some embodiments, the extracellular culture medium and/or cell killed broth contains a mixture of soluble and insoluble enzymes of interest.

5.2.4 Organic Acids

The methods of the invention include contacting cells in a culture medium with organic acid(s) or salt(s) thereof in an amount and under conditions as described herein to inactivate the cells, for example in an amount to effect at least a 4 log, 5 log, 6 log, 7 log or 8 log decrease in amount of viable cells.

In some embodiments, the methods include contacting the cells with a first organic acid (or salt thereof) containing 1 to 5 carbon atoms at about 0.1% to about 15%, 0.2% to about 1%, or about 0.2% to about 0.5% concentration by weight and a second organic acid (or salt thereof) containing 6 or more carbon atoms at about 0.025% to 5% by weight, 0.04% to about 0.3% by weight, or about 0.2% to about 0.5% by weight. In various embodiments, the first organic acid is used at a concentration of any of about 0.2, 0.25, 0.3, 0.35, 0.4, 0.5, 0.55, 0.6, 0.65, 0.7, 0.75, 0.8, 0.85, 0.9, 0.95, or 1% by weight in combination with the second organic acid at a concentration of any of about 0.04, 0.05, 0.06, 0.07, 0.08, 0.09, 0.1, 0.15, 0.2, 0.25, or 0.3, 0.35, 0.4, 0.45, or 0.5% by weight. In one embodiment, the first organic acid is acetic acid at a concentration of about 0.2% to about 0.5% by weight, or about 0.28% by weight and the second organic acid is benzoic acid at a concentration of about 0.04% to about 0.06%, or about 0.044% by weight. In one embodiment, the first organic acid is acetic acid at a concentration of about 0.2% to about 0.5%, or about 0.28% by weight and the second organic acid is benzoic acid at a concentration of about 0.2% to about 0.5%, or about 0.22% by weight.

In some embodiments, the method includes contacting the cells with an organic acid (or salt thereof) containing 6 or more carbon atoms at about 0.25% to about 0.5% by weight. In various embodiments, the organic acid containing 6 or more carbon atoms is used at a concentration of any of about 0.25, 0.3, 0.35, 0.4, 0.45, or 0.5% by weight. In one embodiment, the organic acid containing 6 or more carbon atoms is benzoic acid at a concentration of about 0.5% by weight.

In some embodiments, the organic acid containing 1 to 5 carbon atoms is acetic acid, formic acid, propionic acid (or a salt thereof), or a combination thereof. In one embodiment, the organic acid containing 1 to 5 carbon atoms is acetic acid.

In some embodiments, the organic acid containing 6 or more carbon atoms is benzoic acid, cyclohexanecarboxylic acid, 4-methylvaleric acid, adipic acid, 3-methylglutaric acid, phenylacetic acid (or a salt thereof), or a combination thereof. In one embodiment, the organic acid containing 6 or more carbon atoms is benzoic acid (or a salt thereof, such as sodium benzoate). In some embodiments, the organic acid containing 6 or more carbon atoms contains 6 to 8 (i.e., 6, 7, or 8) carbon atoms. In some embodiments, the organic acid containing 6 or more carbon atoms contains 1 or 2 carboxylic acid functional groups. In some embodiments, the organic acid containing 6 or more carbon atoms is an aromatic organic acid. In some embodiments, the organic acid containing 6 or more carbon atoms contains 7 or 8 carbons and 1 phenyl group.

5.3 Compositions

The invention provides compositions resulting from the methods for killing cells as described herein. In some embodiments, the composition is a cell-killed whole broth containing organic acid(s) as described herein, killed cells and/or cell debris, and culture medium. In some embodiments, the composition contains organic acid(s) as described herein, and optionally further contains killed cells and/or cell debris. In one embodiment, the killed cells and/or cell debris are removed from a cell-killed whole broth as described herein to provide a composition that is free of these components. A cell-killed whole broth or composition of the invention typically contains at least one molecule of interest (e.g., a biomolecule, such as a protein, e.g., an enzyme, and/or an organic substance) produced by the microbial cells which were used to produce the cell-killed whole broth or composition.

Additional preservatives and/or anti-microbial (e.g., bacteriostatic) agents optionally can be added to the cell-killed whole broth or composition, including, but not limited to, sorbitol, sodium chloride, potassium sorbate, and others known in the art.

In some embodiments, the cell-killed whole broth or composition may be supplemented with one or more enzyme activities that are not expressed endogenously, or expressed at relatively low level by the microbial cells. For example, one or more enzymes may be added to improve the degradation of a cellulosic substrate, for example, to fermentable sugars such as glucose or hemi-cellulose sugar (e.g., xylose, arabinose, mannose). The supplemental enzyme(s) can be added as a supplement to the cell-killed whole broth or composition and the enzyme(s) may be a component of a separate fermentation broth, or may be purified, or minimally recovered and/or purified. Suitable, non-limiting examples of supplemental enzymes include cellobiohydrolases, endoglucanase, beta-glucosidase, endo-beta-1,3(4)-glucanase, glucohydrolase, xyloglucanase, xylanase, xylosidase, arabinofuranosidase, alpha-glucuronidase, acetyl xylan esterase, mannanase, mannosidase, alpha-galactosidase, mannan acetyl esterase, galactanase, arabinanase, pectate lyase, pectinase lyase, pectate lyase, polygalacturonase, pectin acetyl esterase, pectin methyl esterase, beta-galactosidase, galactanase, arabinanase, alpha-arabinofuranosidase, rhamnogalacturonase, ferrulic acid esterases rhamnogalacturonan lyase, rhamnogalacturonan acetyl esterase, xylogalacturonosidase, xylogalacturonase, rhamnogalacturonan lyase, lignin peroxidases, manganese-dependent peroxidases, hybrid peroxidases, with combined properties of lignin peroxidases and manganese-dependent peroxidases, glucoamylase, amylase, protease, and laccase.

In some embodiments, the cell-killed whole broth or composition includes cellulolytic enzymes including, but not limited to: (i) endoglucanases (EG) or 1,4-d-glucan-4-glucano-hydrolases (EC 3.2.1.4), (ii) exoglucanases, including 1,4-d-glucan glucanohydrolases (also known as cellodextrinases) (EC 3.2.1.74) and 1,4-d-glucan cellobiohydrolases (exo-cellobiohydrolases, CBH) (EC 3.2.1.91), and (iii) beta-glucosidase (BG) or beta-glucoside glucohydrolases (EC 3.2.1.21).

In some embodiments, the cell-killed whole broth or composition contains one or more enzyme selected from exoglucanase, endoglucanase, hemi-cellulase, and beta-glucosidase.

In one embodiment, the cell-killed whole broth or composition contains about 1000 to about 2000, about 1500 to about 2500, about 2200 to about 2800, or about 2500 CMC U/g endoglucanase activity and about 450 to about 775, about 525 to about 775, about 400 to about 800, or about 650 pNPG U/g beta-glucosidase activity. Carboxymethylcellulose (CMC) activity and para-nitrophenyl-B-D-glucopyranoside (pNPG) activity can be determined using methods known in the art (see for example, Ghose, T. K., "Measurement of Cellulase Activities," *Pure & Appl. Chem.* 59, pp. 257-268, 1987); Chen, H., Hayn, M., Esterbauer, H. "Purification and characterization of two extracellular b-glucosidases from *Trichoderma reesei,*" *Biochimica et Biophysica Acta,* 1992, 1121, 54-60).

In some embodiments, the cell-killed whole broth or composition contains acetic acid at about 0.2% to about 1%, about 0.2% to about 0.5%, or about 0.28% concentration by weight and benzoic acid at about 0.2% to about 0.5%, or about 0.22% concentration by weight, at a pH of about 3.9 to about 4.3, about 3.5 to about 4.5, about 4 to about 5, about 4.5 to about 5.5, about 4.8 to about 5.2, or about 4.

In some embodiments, the cell-killed whole broth or composition contains the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis (e.g., expression of cellulase and/or glucosidase enzyme(s)). In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

The invention also provides a reactive composition that contains a mixture of a cellulosic material, a cell-killed whole broth or composition as described herein, and a fermenting microorganism in a culture medium. In some embodiments, the reactive composition is substantially free of supplemental nitrogen source. In some embodiments, the fermenting microorganism is an ethanologenic microorganism. In some embodiments, production of an organic substance in the reactive composition is increased at least about 50% in comparison to a reactive composition that contains about 1.4% acetic acid and about 0.22% benzoic acid by weight. In one embodiment, the fermenting microorganism is an ethanologenic microorganism, the organic substance is ethanol, and production of ethanol in the reactive composition is increased at least about 10 fold in comparison to a reactive composition that contains about 1.4% acetic acid and about 0.22% benzoic acid by weight.

A cell-killed whole broth or composition as described herein is typically a liquid, but may contain insoluble components, such as killed cells, cell debris, culture media components, and/or insoluble enzyme(s). In some embodiments, insoluble components may be removed to provide a clarified liquid composition.

5.4 Methods of Hydrolyzing Cellulosic Material

The invention provides methods for hydrolyzing a cellulosic material. The method includes contacting a cellulosic material with a cell-killed whole broth or composition resulting from a method for killing cells as described herein, in an amount sufficient to effect enzymatic hydrolysis of the cellulosic material by one or more enzyme(s) in the cell-killed whole broth or composition.

Suitable non-limiting examples of cellulosic substrates include, but are not limited to, biomass, herbaceous material, agricultural residues, forestry residues, municipal solid waste, waste paper, and pulp and paper residues. Common forms of cellulosic substrate for use in the present invention include, but are not limited to trees, shrubs and grasses, wheat, wheat straw, sugar cane bagasse, corn, corn husks, corn kernel including fiber from kernels, products and by-products from milling of grains such as corn (including wet milling and dry milling) as well as municipal solid waste, waste paper and yard waste. The cellulosic substrate may be obtained from "virgin biomass" (such as trees, bushes, grasses, fruits, flowers, herbaceous crops, hard and soft woods), "non-virgin biomass" (such as agricultural byproducts, commercial organic waste, construction and demolition debris, municipal solid waste and yard waste), or "blended biomass," which is a mixture of virgin and non-virgin biomass.

In some embodiments, the cellulosic substrate includes wood, wood pulp, papermaking sludge, paper pulp waste streams, particle board, corn stover, corn fiber, rice, paper and pulp processing waste, woody or herbaceous plants, fruit pulp, vegetable pulp, pumice, distillers grain, grasses, rice hulls, sugar cane bagasse, cotton, jute, hemp, flax, bamboo, sisal, abaca, straw, corn cobs, distillers grains, leaves, wheat straw, coconut hair, algae, switchgrass, and mixtures thereof.

The cellulosic substrate can be used as is or may be subjected to pretreatment using conventional methods known in the art. Such pretreatments include chemical, physical, and biological pretreatment. For example, physical pretreatment techniques can include without limitation various types of milling, crushing, steaming/steam explosion, irradiation and hydrothermolysis. Chemical pretreatment techniques can include without limitation dilute acid, alkaline, organic solvent, ammonia, sulfur dioxide, carbon dioxide, and pH-controlled hydrothermolysis. Biological pretreatment techniques can include without limitation applying lignin-solubilizing microorganisms.

5.5 Methods of Producing Organic Substances in Microorganisms

The invention provides methods for producing organic substances in microorganisms, e.g., fermenting microorganisms. The methods include producing hydrolyzed cellulosic material with a cell-killed whole broth or composition, as described above, and growing a fermenting microorganism in the presence of the hydrolyzed cellulosic material under conditions suitable for the fermenting microorganism to produce one or more organic substance(s) of interest. In some embodiments, the fermenting microorganism is an ethanologenic microorganism and the method is used to produce ethanol. In some embodiments, a pretreated cellulosic material is used.

Hydrolysis of the cellulosic material and fermentation of the fermenting microorganism to produce an organic substance may occur simultaneously or sequentially.

In some embodiments, use of a cell-killed whole broth or compositions described herein increases production of an organic substance by at least about 50% in comparison to a method in which the cellulosic material on which the fermenting microorganism is grown is hydrolyzed with a composition that contains about 1.4% acetic acid and about 0.22% benzoic acid by weight. In some embodiments, production of an organic substance (e.g., ethanol or another organic molecule) is increased at least about 0.5, 1, 2, 3, 4, 5, 6, 7, 8, 9, or fold in comparison to a method in which the cellulosic material on which the fermenting microorganism is grown is hydrolyzed with a composition that contains about 1.4% acetic acid and about 0.22% benzoic acid by weight.

Suitable fermenting microorganisms are able to ferment or convert sugars, such as glucose, xylose, galactose, arabinose, mannose, or oligosaccharides, into the desired fermentation product or products. Suitable non-limiting examples of fermenting microorganisms include fungal organisms, such as yeast, and bacteria.

In some embodiments, the fermenting microorganism is an ethanologenic microorganism, such as a naturally occurring ethanologenic organism, an ethanologenic organism with naturally occurring or induced mutations, or an ethanologenic organism that has been genetically modified.

In some embodiments, the ethanologenic microorganism is a yeast cell, such as *Saccharomyces cerevisiae, S. uvarum, Kluyveromyces fagilis, candida pseudotropicalis*, and *Pachysolen tannophilus*, that can efficiently ferment glucose to ethanol. Suitable strains include, but are not limited to, *S. cerevisiae* $D_{5A}$ (ATCC200062), *S. cerevisiae* Y567 (ATCC24858), ACA 174 (ATCC 60868), MY91 (ATCC 201301), MY138 (ATCC 201302), C5 (ATCC 201298), ET7 (ATCC 201299), LA6 (ATCC 201300), OSB21 (ATCC 201303), F23 (*S. globosus* ATCC 90920), ACA 174 (ATCC 60868), A54 (ATCC 90921), NRCC 202036 (ATCC 46534), ATCC 24858, ATCC 24858, G 3706 (ATCC 42594), NRRL, Y-265 (ATCC 60593), Sa28 (ATCC 26603), and ATCC 24845-ATCC 24860. Other non-*cerevisiae* yeast strains suitable for use in the present invention include *Pichia pastoris* (tozony ID 4922), *S. pastorianus* SA 23 (*S. carlsbergensis* ATCC 26602), *S. pastorianus* (*S. carlsbergensis* ATCC 2345), *Candida acidothermophilum* (*Issatchenkia orientalis*, ATCC 20381). In some embodiments, the ethanologenic microorganism is a recombinant yeast strain. Suitable recombinant yeast may contain genes encoding xylose reductase, xylitol dehydrogenase and/or xylulokinase (see for example, U.S. Pat. No. 5,789,210).

In some embodiments, the ethanologenic microorganism is a bacterial cell, for example, a Gram-negative, facultatively anaerobic bacterial cell, such as a bacterial cell from the family Enterobacteriaceae. In some embodiments, the ethanologenic microorganism is from the genus *Escherichia* or *Klebsiella* and, for example, *E. coli* B, *E. coli* DH5α, *E. coli* KO4 (ATCC 55123), *E. coli* KO11 (ATCC 55124), *E. coli* KO12 (ATCC 55125), *E. coli* LY01, *K. oxytoca* M5A1, or *K. oxytoca* P2 (ATCC 55307). In some embodiments, the ethanologenic microorganism is a *Zymomonas* species, or derived from *Zymomonas mobilis* (ATCC31821). In some embodiments, a recombinant *Zymomonas* strain may contain genes encoding xylose isomerase, xylulokinase, transaldolase and transketolase, for example.

While hydrolyzing the cellulosic material to glucose and other small saccharides is an important step, simultaneous saccharification and fermentation (SSF) relies upon a live culture of an ethanologenic microorganism to transform these sugars to ethanol.

Fermenting microorganisms are typically added to the hydrolysate and the fermentation is allowed to proceed for 12-96 hours, such as 30-80 hours. The temperature is typically 26-40° C., for example, about 32° C., and the pH is typically 3-6.

Following the fermentation, the organic substance of interest is recovered by any method known in the art. Such methods include, but are not limited to distillation, extraction, chromatography, electrophoretic procedures, and differential solubility. For example, in an ethanol fermentation, the alcohol may be separated and purified by conventional methods of distillation. The ethanol obtained according to the process of the invention may be used as fuel ethanol, drinking ethanol or as industrial ethanol.

While not being bound to a theory of the invention, it is believed that unclarified, cell-killed whole broth provides residual nutrients to the ethanologenic microorganism. This may lead to faster ethanol fermentation and improve ethanol yields. The ability to eliminate the need to provide a nutrient broth, or reduce the amount of supplemental nutrients, to the ethanologenic microorganism in addition to the saccharified cellulose, results in decreased cost of raw materials for the ethanol fermentation process.

In some embodiments, using a cell-killed whole broth or composition as described herein in a method for production of an organic substance in a fermenting microorganism can reduce the amount and/or type of supplemental nitrogen source for the fermenting microorganism. In some embodiments, the methods and compositions of the present invention can reduce the amount of yeast extract, peptone, and/or urea required for growth of the fermenting microorganism.

In some embodiments, a method for producing an organic substance in a fermenting microorganism as described herein is absent or substantially free of supplemental nitrogen and/or nutrient source for the fermenting microorganism. In some embodiments, the methods and compositions are absent or substantially free of yeast extract, peptone, and/or urea. It is understood to one of ordinary skill in the art that the methods and compositions of the invention can be absent or substantially free of supplemental nitrogen source, however, trace amounts of nitrogen and/or nutrient source may be present as impurities or added in such an amount that would not substantially increase the nutrient value of the whole fermentation broth to the fermenting microorganism.

In one embodiment, the invention provides a method for producing an organic substance by simultaneous saccharification and fermentation. The method includes combining, in the absence of a supplemental nitrogen sources, a cellulosic material (e.g., a pretreated cellulosic material), a cell-killed whole broth or composition as described herein that contains one or more enzyme(s) capable of hydrolyzing the cellulosic material (e.g., exoglucanase, endoglucanse, hemi-cellulase, and/or beta-glucosidase), and a fermenting microorganism. The cellulosic material, cell-killed whole broth or composition, and fermenting microorganism are incubated under conditions conducive both to hydrolysis of cellulose to glucose and/or hemi-cellulose sugar (e.g., xylose, arabinose, and/or mannose) and to conversion of glucose and/or hemi-cellulose sugar to the organic substance. In some embodiments, production of an organic substance is increased at least about 50% in comparison to a method in which a cell-killed whole broth or composition is used that contains about 1.4% acetic acid and about 0.22% benzoic acid by weight. In one embodiment, the fermenting microorganism is an ethanologenic microorganism, the organic substance is ethanol, and production of ethanol is increased at least about 10 fold in comparison to a method in which a cell-killed whole broth or composition is used that contains about 1.4% acetic acid and about 0.22% benzoic acid by weight. In one embodiment, a cell-killed whole broth is used that contains about 1000 to about 2000, about 1500 to about 2500, about 2200 to about 2800, or about 2500 CMC U/g endoglucanase activity and about 450 to about 775, about 525 to about 775, about 400 to about 800, or about 650 pNPG U/g beta-glucosidase activity, about 0.2% to about 1%, about 0.2% to about 0.5%, or about 0.28% acetic acid by weight, about 0.2% to about 0.5%, or about 0.22% benzoic acid by weight (or about 0.26% sodium benzoate), at a pH of about 3.9 to about 4.3, about 3.5 to about 4.5, about 4, to about 5, about 4.5 to about 5.5, about 4.8 to about 4.2, or about 4.

5.6 Kits

The invention also provides kits. Kits of the invention contain a cell-killed whole broth or composition containing a combination of organic acids as described herein. Suitable packaging is provided. As used herein, "packaging" refers to a solid matrix, material, or container customarily used in a system and capable of holding within fixed limits components of a kit as described herein.

A kit also may contain instructions for use of the cell-killed whole broth or composition. For example, instructions may be provided for use of the cell-killed whole broth or composition in a method for hydrolysis of a cellulosic substrate or instructions for use in a method for producing an organic substance in a fermenting microorganism, as described herein. Instructions may be provided in printed form or in the form of an electronic medium such as a floppy disc, CD, or DVD, or in the form of a website address where such instructions may be obtained.

5.7 Specific Embodiments

In one aspect, the invention provides a method of killing cells in a fermentation culture. The method includes contacting a fermentation culture that contains the cells in a culture medium with a first organic acid containing 1 to 5 carbon atoms or a salt thereof and a second organic acid containing 6 or more carbon atoms or a salt thereof. In one embodiment, the concentration of the first organic acid is about 0.2% to about 1% by weight and the concentration of the second organic acid is about 0.04% to about 0.3% by weight. In one embodiment, the concentration of the first organic acid is about 0.2% to about 0.5% by weight and the concentration of the second organic acid is about 0.2% to about 0.5% by weight. The method proceeds for a period of time and at a temperature and pH sufficient to effect substantially complete cell kill, thereby producing a cell-killed whole broth. In some embodiments, the period of time is about 8 to about 24 hours, the temperature is about 30° C. to about 40° C., and the pH is about 3.5 to about 4.5, about 3.9 to about 4.2, or about 4 to about 4.4. In one embodiment, the period of time is about 24 hours, the temperature is about 40° C., and the pH is about 4. Substantially complete cell kill typically involves at least about a 4 log, 5 log, 6 log, 7 log, or 8 log decrease in viable cells.

In some embodiments of the method of killing cells, the cells are microbial cells (i.e., fungal or bacterial). In some embodiments, the cells are fungal cells, for example, filamentous fungal cells. In some embodiments, the cells are filamentous fungal cells are selected from *Trichoderma, Aspergillus, Penicillium, Humicola, Chrysosporium*, and *Neurospora*.

In some embodiments of the method of killing cells, the first organic acid is selected from acetic acid, formic acid, or propionic acid. In one embodiment, the first organic acid is acetic acid. In some embodiments, the second organic acid is selected from benzoic acid, cyclohexanecarboxylic acid, 4-methylvaleric acid, and phenylacetic acid. In one embodiment, the second organic acid is benzoic acid. In some embodiments, a salt of an organic acid is used, for example, sodium benzoate. In one embodiment, the first organic acid is acetic acid at a concentration of about 0.28% by weight and the second organic acid is benzoic acid at a concentration of about 0.044% by weight (or sodium benzoate at a concentration of about 0.052% by weight). In one embodiment, the first organic acid is acetic acid at a concentration of about 0.28% by weight and the second organic acid is benzoic acid at a concentration of about 0.22% by weight (or sodium benzoate at a concentration of about 0.26% by weight).

In some embodiments of the method of killing cells, the cells secrete at least one enzyme of interest extracellularly into the culture medium. In some embodiments, the enzyme of interest is expressed recombinantly. In some embodiments, the cells secrete at least one enzyme of interest selected from exoglucanase, endoglucanase, hemi-cellulase, and beta-glucosidase.

In another aspect, the invention provides a cell-killed whole broth produced by any of the methods for killing cells described herein. In one embodiment, the cell-killed whole broth contains one or more enzyme that was secreted by the cells into the extracellular culture medium prior to killing the cells. In some embodiments, the cell-killed whole broth contains at least one enzyme selected from exoglucanase, endoglucanase, hemi-cellulase, and beta-glucosidase in the extracellular culture medium. In some embodiments, the cell-killed whole both contains about 1000 to about 2000, about 1500 to about 2500, about 2200 to about 2800, or about 2500 CMC U/g endoglucanase activity and about 450 to about 775, about 525 to about 775, about 400 to about 800, or about 650 pNPG U/g beta-glucosidase activity. In one embodiment, the composition contains about 2200 to about 2800 CMC U/g endoglucanase activity and about 450 to about 775 pNPG U/g beta-glucosidase activity at a pH of about 3.9 to about 4.3.

In some embodiments, production of an organic substance by a fermenting microorganism is increased at least about 50% in the presence of the cell-killed whole broth in comparison to a method in which a cell-killed whole broth that contains about 1.4% acetic acid and about 0.22% benzoic acid by weight is used. In one embodiment, the fermenting microorganism is an ethanologenic microorganism. In one embodiment, production of ethanol by a fermenting ethanologenic organism is increased at least about 10 fold in comparison to a method in which a cell-killed whole broth that contains about 1.4% acetic acid and about 0.22% benzoic acid by weight is used.

In another aspect, the invention provides a composition containing a first organic acid containing 1 to 5 carbon atoms or a salt thereof and a second organic acid containing 6 or more carbon atoms or a salt thereof, and an enzyme of interest. In some embodiments, the composition also contains killed cells and culture medium, wherein the cells were grown in the culture medium and produced the enzyme of interest prior to contact with the first and second organic acids. In one embodiment, the first organic acid is present in the composition at a concentration of about 0.2% to about 1% by weight, and the second organic acid is present at a concentration of about 0.04% to about 0.3% by weight. In one embodiment, the first organic acid is present in the composition at a concentration of about 0.2% to about 0.5% by weight, and the second organic acid is present at a concentration of about 0.2% to about 0.5% by weight. In some embodiments, the first organic acid is selected from acetic acid, formic acid, or propionic acid. In one embodiment, the first organic acid is acetic acid. In some embodiments, the second organic acid is selected from benzoic acid, cyclohexanecarboxylic acid, 4-methylvaleric acid, and phenylacetic acid. In one embodiment, the second organic acid is benzoic acid. In some embodiments, a salt of an organic acid is used, for example, sodium benzoate. In one embodiment, the first organic acid is acetic acid at a concentration of about 0.28% by weight and the second organic acid is benzoic acid at a concentration of about 0.044% by weight (or sodium benzoate at a concentration of about 0.052% by weight). In one embodiment, the first organic acid is acetic acid at a concentration of about 0.28% by weight and the second organic acid is benzoic acid at a concentration of about 0.22% by weight (or sodium benzoate at a concentration of about 0.26% by weight). In some embodiments, the composition contains one or more enzyme selected from exoglucanase, endoglucanase, hemi-cellulase, and beta-glucosidase. In one embodiment, the compositions contains about 1000 to about 2000, about 1500 to about 2500, about 2200 to about 2800, or about 2500 CMC U/g endoglucanase activity and about 450 to about 775, about 525 to about 775, about 400 to about 800, or about 650 pNPG U/g beta-glucosidase activity. In some embodiments, the pH is about 3.9 to about 4.3, about 3.5 to about 4.5, about 4 to about 5, about 4.5 to about 5.5, about 4.8 to about 5.2, or about 4. In one embodiment, the composition contains about 2200 to about 2800 CMC U/g endoglucanase activity and about 450 to about 775 pNPG U/g beta-glucosidase activity at a pH of about 3.9 to about 4.3.

In another aspect, the invention provides a method of hydrolyzing a cellulosic material, including contacting the cellulosic material with a cell-killed whole broth produced by a method of killing cells as described herein or a composition containing a first organic acid containing 1 to 5 carbon atoms or a salt thereof, a second organic acid containing 6 or more carbon atoms or a salt thereof, and at least one enzyme of interest as described herein in an amount effective to cause enzymatic hydrolysis of cellulosic material by one or more enzyme in the cell-killed whole broth or composition. In some embodiments, a composition is used that further includes a culture medium and killed cells, wherein the cells were grown in the culture medium and produced the enzyme of interest prior to contact with the first and second organic acids. In some embodiments, the cellulosic material is a plant biomass material. In one embodiment, the cellulosic material is a lignocellulosic material. In some embodiments, the cellulosic material is pretreated to enhance enzymatic hydrolysis. The invention also provides a hydrolyzed cellulosic material produced by hydrolysis with a cell-killed whole broth produced by a method of killing cells as described herein or a composition containing a first organic acid containing 1 to 5 carbon atoms or a salt thereof, a second organic acid containing 6 or more carbon atoms or a salt thereof, at least one enzyme of interest, and optionally a fermentation culture medium and killed cells, as described herein.

In another aspect, the invention provides a method of producing an organic substance. The method includes fermenting a microorganism that produces an organic substance in a culture medium in the presence of a hydrolyzed cellulosic material produced by hydrolysis with a cell-killed whole broth produced by a method of killing cells as described herein or a composition containing a first organic acid containing 1 to 5 carbon atoms or a salt thereof, a second organic acid containing 6 or more carbon atoms or a salt thereof, at least one enzyme of interest, and optionally a fermentation culture medium and killed cells as described herein, under conditions suitable for the microorganism to produce the organic substance. In one embodiment, the microorganism is an ethanologenic microorganism and the organic substance is ethanol. In one embodiment, the concentration of the organic substance in the culture medium is increased at least about 50% in comparison to a method in which the cellulosic material is hydrolyzed with a cell-killed whole broth or composition that contains similar, substantially identical, or identical components to the cell-killed whole broth or composition used in the method with the exception that the cell-killed whole broth or composition contains about 1.4% acetic acid and about 0.22% benzoic acid by weight. In one embodiment, production of ethanol by a fermenting ethanologenic organism is increased at least about 10 fold in comparison to a method in which a cell-killed whole broth or composition that contains about 1.4% acetic acid and about 0.22% benzoic acid by weight is used.

In some embodiments, enzymatic hydrolysis of the cellulosic material and fermentation of the microorganism occur simultaneously. In other embodiments, enzymatic hydrolysis of the cellulosic material occurs prior to fermentation of the microorganism.

In another aspect, the invention provides a method of producing an organic substance by simultaneous saccharification and fermentation. The method includes (a) combining, in the absence of a supplemental nitrogen source, a cellulosic substrate, a cell-killed whole broth produced by a method of killing cells as described herein or a composition containing a first organic acid containing 1 to 5 carbon atoms or a salt thereof, a second organic acid containing 6 or more carbon atoms or a salt thereof, at least one enzyme of interest, and optionally a fermentation culture medium and killed cells as described herein, and a fermenting microorganism; and incubating the cellulosic substrate, the cell-killed whole fermentation broth or composition, and the fermenting microorganism in a culture medium under conditions conducive both to hydrolysis of cellulose to glucose and/or hemi-cellulose sugar (e.g., xylose, arabinose, and/or mannose) and to conversion of glucose and/or hemi-cellulose to the organic substance, wherein concentration of the organic substance in the culture medium is increased at least about 50% in comparison to a method in which the cellulosic material is hydrolyzed with a cell-killed whole broth or composition that contains similar, substantially identical, or identical components to the cell-killed whole broth or composition used in the method with the exception that the cell-killed whole broth or composition contains about 1.4% acetic acid and about 0.22% benzoic acid by weight. In one embodiment, the fermenting microorganism is an ethanologenic microorganism and the organic substance is ethanol. In one embodiment, production of ethanol by a fermenting ethanologenic organism is increased at least about 10 fold in comparison to a method in which a cell-killed whole broth or composition that contains about 1.4% acetic acid and about 0.22% benzoic acid by weight is used.

In another aspect, the invention provides a reactive composition for production of an organic substance. The reactive composition contains a mixture of a cellulosic substrate, a cell-killed whole broth produced by a method of killing cells as described herein or a composition containing a first organic acid containing 1 to 5 carbon atoms or a salt thereof, a second organic acid containing 6 or more carbon atoms or a salt thereof, at least one enzyme of interest, and optionally a fermentation culture medium and killed cells as described herein, and a fermenting microorganism in a culture medium. The reactive composition is substantially free of supplemental nitrogen source, and concentration of the organic substance in the culture medium is increased at least about 50% in comparison to a method in which the cellulosic material is hydrolyzed with a cell-killed whole broth or composition that contains similar, substantially identical, or identical components to the cell-killed whole broth or composition used in the method with the exception that the cell-killed whole broth or composition contains about 1.4% acetic acid and about 0.22% benzoic acid by weight. In one embodiment, the fermenting microorganism is an ethanologenic microorganism and the organic substance is ethanol. In one embodiment, production of ethanol by a fermenting ethanologenic organism is increased at least about 10 fold in comparison to a composition that contains a cell-killed whole broth or composition with about 1.4% acetic acid and about 0.22% benzoic acid by weight.

In another aspect, the invention provides kits containing a cell-killed whole broth produced by a method of killing cells as described herein or a composition containing a first organic acid containing 1 to 5 carbon atoms or a salt thereof, a second organic acid containing 6 or more carbon atoms or a salt thereof, at least one enzyme of interest, and optionally a fermentation culture medium and killed cells as described herein, in packaging. In some embodiments, the kit further contains instructions for use in a method for producing an organic substance with a fermenting microorganism, for example, instructions for use in a method for producing ethanol with an ethanologenic microorganism and a cellulosic substrate hydrolyzed with the cell-killed whole broth or composition in the kit.

The following examples are intended to illustrate, but not limit, the invention.

6. EXAMPLES

Example 1

Cell Kill Conditions

Determination of Fungal Cell Count

An aliquot from a 150 hour fermentation of *Trichoderma reesei* was serially diluted with sterile water to a dilution factor of $10^3$. A sample of 100 µl of the dilution was then spread plated onto potato dextrose agar (PDA) purchased from Difco™ (REF#213200) and incubated at 25° C. The incubated PDA plate was then counted for colony forming units (CFU) after 3 days of incubation. A CFU is characterized as a separate, individual cluster of growing cells present on agar, and the number of these CFU present on agar multiplied by the degree of the dilution plated is the number of CFU present in the original sample.

Separate spore suspensions of *Aspergillus niger* and *Penicillium funiculosum* were spread plated on PDA purchased from Difco™ (REF#213200) and incubated at 25° C. for 3 days. Separate sections of PDA containing *A. niger* and *P. funiculosum* colonies were then removed aseptically and placed into separate shake flasks containing yeast extract glucose (YEG) media consisting of 5 g/L yeast extract and 20 g/L glucose. The shake flasks were then incubated on a rotary shaker set at 200 rpm and 33° C. for 3 days. Samples of the growth cultures were removed and serially diluted with sterile water to a dilution factor of $10^4$. A sample of 100 µl of the dilution was then spread plated onto PDA and incubated at 25° C. The incubated PDA plates were then counted for CFU.

*T. reesei* Cell Kill with Acetic Acid and Sodium Benzoate at Different Temperatures

*Trichoderma reesei* fermentation broth was separated into 5 aliquots and formulated as described in table 1 below. The formulated broth was then pH adjusted to 4.0 using 10% (w/w) sulfuric acid. Each formulation was then further separated into 3 aliquots with one aliquot at 10° C. incubation, another aliquot at 25° C. incubation, and the third aliquot at 40° C. incubation. After 24 hours of incubation all aliquots were pH adjusted to 4.8 using 10% (w/w) sodium hydroxide. Each aliquot was then serially diluted with sterile water, spread plated onto PDA, and incubated at 25° C. The incubated PDA plates were then counted for CFU.

TABLE 1

Formulation description of *T. reesei* fermentation broth.

| Aliquot # | Formulation |
| --- | --- |
| 1 | 11.2 g/L acetic acid, 2.06 g/L sodium benzoate |
| 2 | 8.4 g/L acetic acid, 1.55 g/L sodium benzoate |

TABLE 1-continued

Formulation description of *T. reesei* fermentation broth.

| Aliquot # | Formulation |
| --- | --- |
| 3 | 5.6 g/L acetic acid, 1.03 g/L sodium benzoate |
| 4 | 2.8 g/L acetic acid, 0.52 g/L sodium benzoate |
| 5 | 20 g/L acetic acid |

Figure 1:
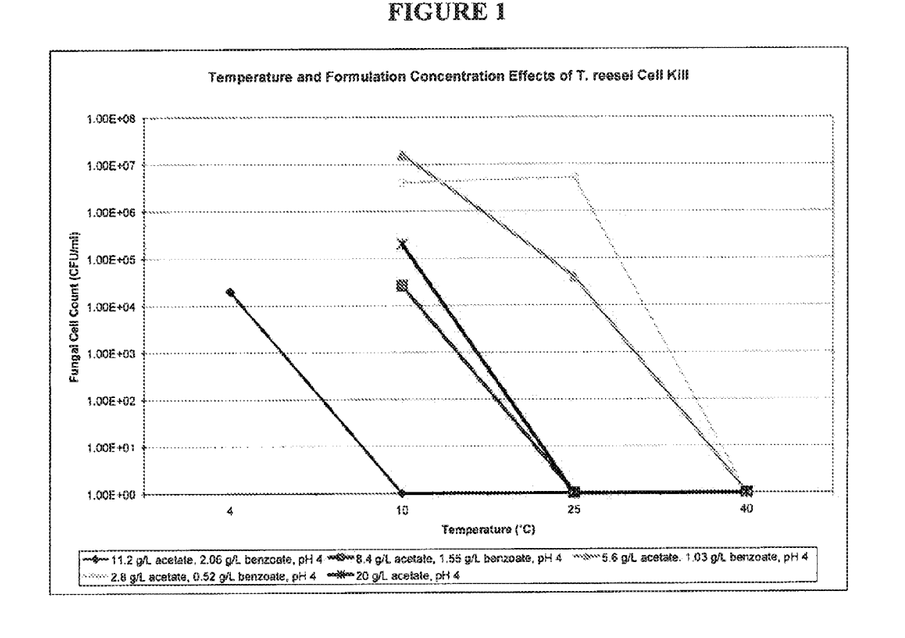
FIG. 1 shows the effects of temperature and formulation chemical concentration on *T. reesei* cell kill.

Complete cell kill was achieved at a temperature of 40° C. for all formulations. *T. reesei* cell kill could be achieved at lower temperatures but required higher concentrations of the organic acids. FIG. 1 is a graph illustrating the effects of temperature and formulation chemical concentration on *T. reesei* cell kill.

Effect of Sodium Benzoate

Figure 2:
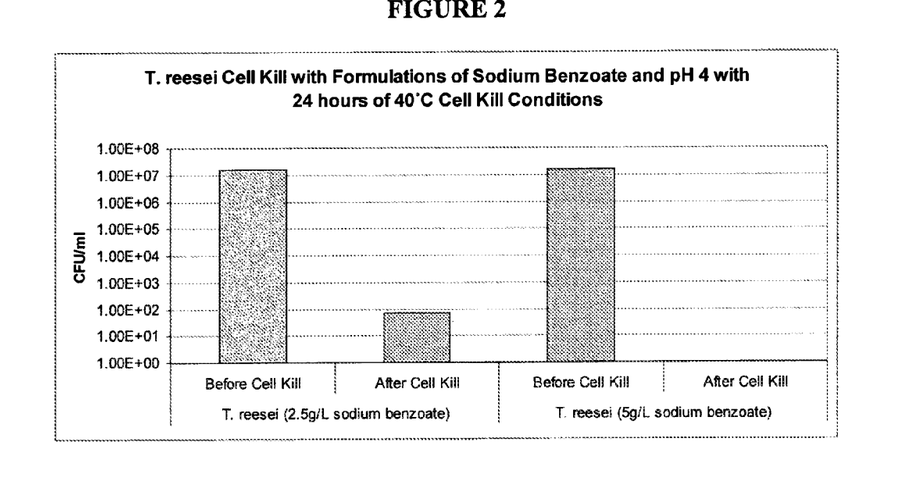
FIG. 2 shows the effect of sodium benzoate concentration on *T. reesei* cell kill at 40° C. and pH 4.

Sodium benzoate was added to separate *T. reesei* aliquots to a final concentration of 2.5 g/L sodium benzoate or 5 g/L sodium benzoate. The aliquots were then adjusted to pH 4 and incubated for 24 hours at 40° C. After 24 hours of incubation all aliquots were pH adjusted to 4.8 using 10% (w/w) sodium hydroxide. Each aliquot was then serially diluted with sterile water, spread plated onto PDA, and incubated at 25° C. The incubated PDA plates were then counted for CFU. The results are shown in FIG. 2.

*T. reesei* formulated with 2.5 g/L sodium benzoate, pH 4, experienced a 5 log reduction of viable cells after 24 hours of 40° C. incubation, while a *T. reesei* formulation of 5 g/L sodium benzoate, pH 4 experienced a 7 log reduction with less than 10 CFU present after 24 hours of 40° C. incubation.

Application of Cell Kill Conditions to *A. niger* and *P. funiculosum* Cultures

Figure 3:
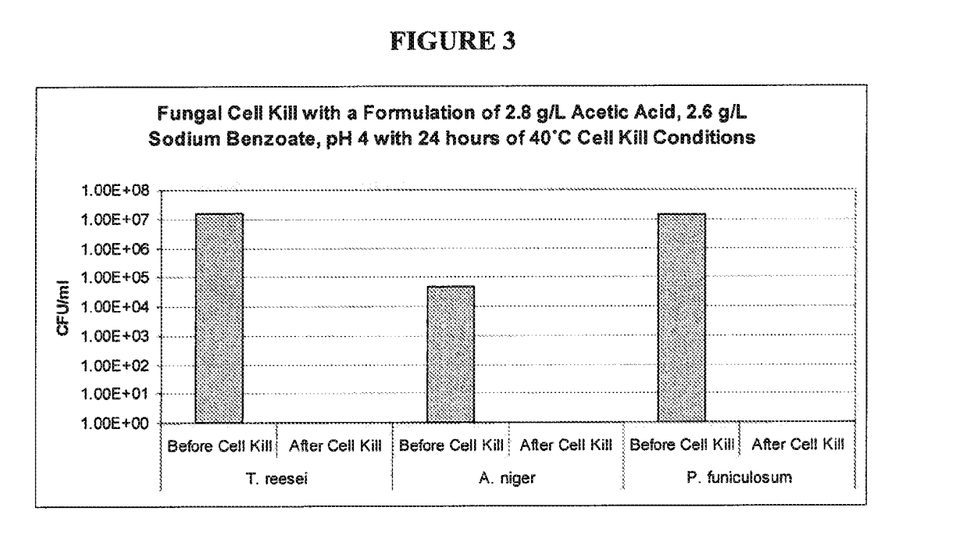
FIG. 3 shows the effect of cell kill conditions on fungal cell kill.

Acetic acid and sodium benzoate were added to separate aliquots of *T. reesei*, *A. niger* and *P. funiculosum* growth cultures to a final concentrations of 2.8 g/L and 2.6 g/L, respectively. The aliquots were then adjusted to pH 4 and incubated for 24 hours at 40° C. After 24 hours of incubation all aliquots were pH adjusted to 4.8 using 10% (w/w) sodium hydroxide. Each aliquot was then serially diluted with sterile water, spread plated onto PDA, and incubated at 25° C. The incubated PDA plates were then counted for CFU. The results are shown in FIG. 3.

Figure 4:
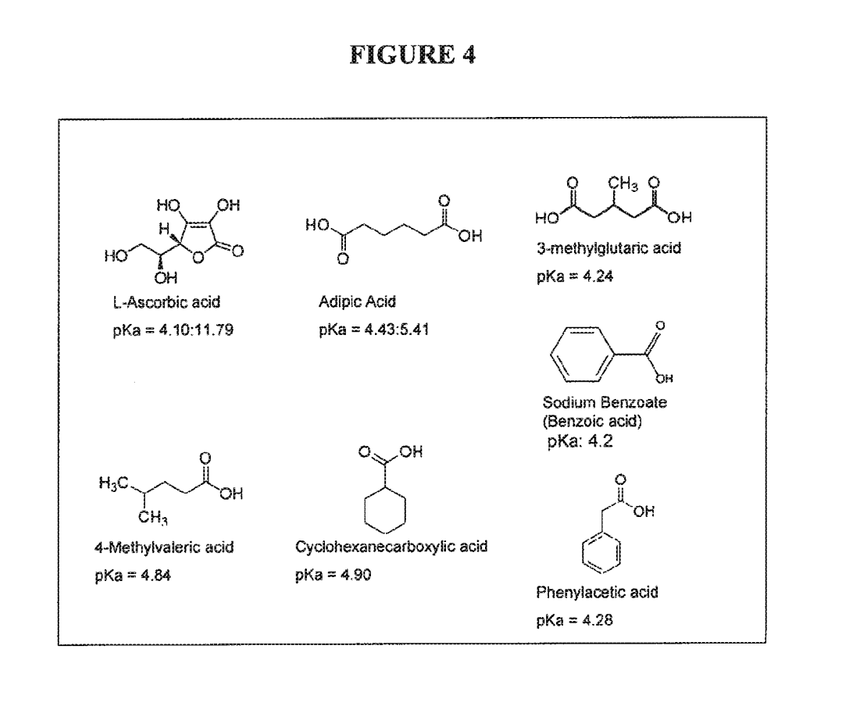
FIG. 4 shows chemical structures and pKa values for organic acids with 6 or more carbons.

After 24 hours of exposure to cell kill conditions no viable cells were present from *T. reesei*, *A. niger* and *P. funiculosum*. Cell Kill with Organic Acids Having Six or More Carbon A separate unformulated aliquot of *T. reesei* fermentation broth was further separated into 10 aliquots and formulated with organic acids having 6 or more carbons as described in table 2 below. Chemical structures and pKa's of the organic acids are shown in FIG. 4.

TABLE 2

Formulation of *T. reesei* Fermentation Broth with Organic Acids having Six or More Carbon Atoms

| *T. reesei* Aliquot # | Formulation Composition |
| --- | --- |
| 1 | 5 g/L cyclohexanecarboxylic acid |
| 2 | 15 g/L cyclohexanecarboxylic acid |
| 3 | 5 g/L L-ascorbic acid |
| 4 | 15 g/L L-ascorbic acid |
| 5 | 5 g/L adipic acid (pH 5) |
| 6 | 15 g/L adipic acid (pH 5) |
| 7 | 5 g/L 4-methylvaleric acid |
| 8 | 15 g/L 4-methylvaleric acid |
| 9 | 5 g/L 3-methylglutaric acid |
| 10 | 15 g/L 3-methylglutaric acid |

TABLE 2-continued

Formulation of *T. reesei* Fermentation Broth with Organic Acids having Six or More Carbon Atoms

| T. reesei Aliquot # | Formulation Composition |
|---|---|
| 11 | 5 g/L phenylacetic acid |

Figure 5:
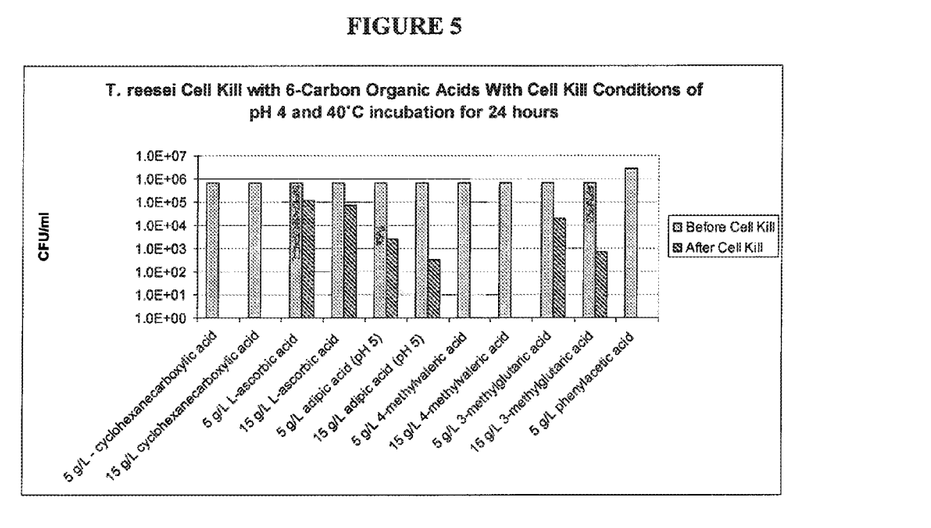
FIG. 5 shows the effects of different organic acids with 6 or more carbons on *T. reesei* cell kill at 40° C. and pH 4.

The formulated cultures were then pH adjusted to 4.0 using 10% (w/w) sulfuric acid. The formulated cultures were then incubated at 40° C. After 2 and 4 hours of incubation, the pH of the formulated cultures were measured and adjusted to 4.0 with 10% (w/w) sulfuric acid and returned to 40° C. incubation. After 24 hours of incubation the formulated cultures were removed and 100 μl of formulated culture was then spread plated at dilutions of $10^0$, $10^1$, $10^2$ and $10^3$ onto PDA and incubated at 25° C. The incubated PDA plates were then counted for CFU. The results are shown in FIG. 5.

Example 2

Effect of Cell-Killed Whole Broth on Production of Organic Substances in Microorganisms Cell-killed whole broth was prepared from a fermentation culture of *T. reesei* cells that secrete exoglucanase, endoglucanase, hemi-cellulase, and beta-glucosidase enzymes into the extracellular medium. The fermentation culture was treated with 0.28% acetic acid and 0.052% sodium benzoate by weight at pH 4 and 40° C. for 24 hours as described in Example 1 ("Broth A") or 1.4% acetic acid, 0.26% sodium benzoate, and 0.5% potassium sorbate by weight at pH 4 and 10° C. for 24 hours ("Broth B"). The effects of these two broths on fermentation of a microorganism to produce an organic substance were investigated. The broths were used to hydrolyze a cellulosic substrate to produce a glucan hydrolysate for use as a carbon source for growth of the microorganism. Production of organic substances by microorganisms grown on the glucan hydrolysate was assessed.

Hydrolysate Generation

Pretreated bagasse was obtained from the National Renewable Energy Laboratory (NREL). The bagasse was pretreated with dilute sulfuric acid and increasing temperature by NREL (Schell et al. (2004) *Bioresource Technology* 91, 179-188). The acid pretreated bagasse was then washed with deionized water until the pH was greater than 4.2, after which the residual water was removed by vacuum filtration. The washed acid pretreated bagasse (wAPB) was then autoclaved for 20 minutes at 121° C. to remove any microbial contaminants from the wAPB substrate. A 13% (w/w) glucan hydrolysate was then generated from the autoclaved wAPB using an 80 mg protein dose of Broth A or Broth B per gram of substrate glucan. Each hydrolysate was generated under saccharification conditions consisting of 5 days of incubation at 50° C. in a rotary shaker set to 200 rpm. The glucose concentration of each hydrolysate was than analyzed following the procedure outlined below in the HPLC assay section. Following saccharification of the wAPB, each hydrolysate was separated into 3 flasks and diluted with sterile filtered 50 mM sodium citrate buffer (pH 4.8) to create 1% (w/w) glucan, 7% (w/w) glucan, and a 13% (w/w) glucan hydrolysate mixtures.

*Lactobacillus rhamnosus* Culture Preparation

Lyophilized *Lactobacillus rhamnosus* (ATCC7469) was obtained from American Type Culture Collection (ATCC) and was rehydrated with sterile water. The rehydrated *L. rhamnosus* was then spread plated on to *Lactobacilli* MRS Agar purchased from Difco™ (REF#288210) and incubated for 2 days at 37° C. to obtain *L. rhamnosus* colonies. *L. rhamnosus* colonies were then aseptically added into a shake flask containing *Lactobacilli* MRS Broth purchased from Difco™ (REF#288130). The *L. rhamnosus* shake flask was then incubated in a rotary shaker set to 33° C. and 150 rpm for 1 day to obtain a growth culture.

*L. rhamnosus* Hydrolysate Fermentation

Figure 6:
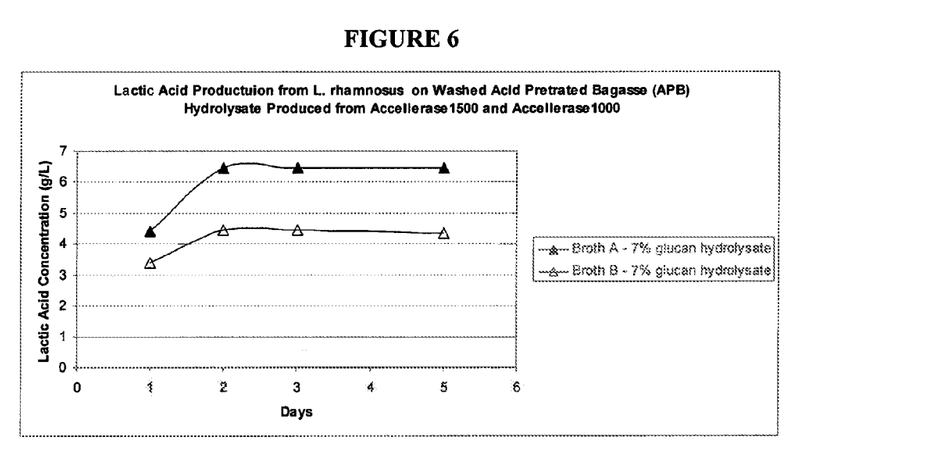
FIG. 6 shows lactic acid production from *L. rhamnosus* on washed APB hydrolysate as described in Example 2.

A growth culture of *L. rhamnosus* was inoculated at a concentration of 3% (v/w) into separate hydrolysate flasks with wAPB at 7% (w/w) glucan produced with Broths A and B. The *L. rhamnosus* inoculated flasks were fermented under anaerobic conditions in a rotary shaker set to 37° C. and 150 rpm for 5 days. The fermentation mixtures were sampled after 1, 2, 3, and 5 days of incubation and analyzed for lactic acid and glucose concentrations following the procedure outlined below in the HPLC assay section. The results are shown in FIG. 6.

Thermosacc Yeast Simultaneous Saccharification and Fermentation (SSF)

Figure 7:
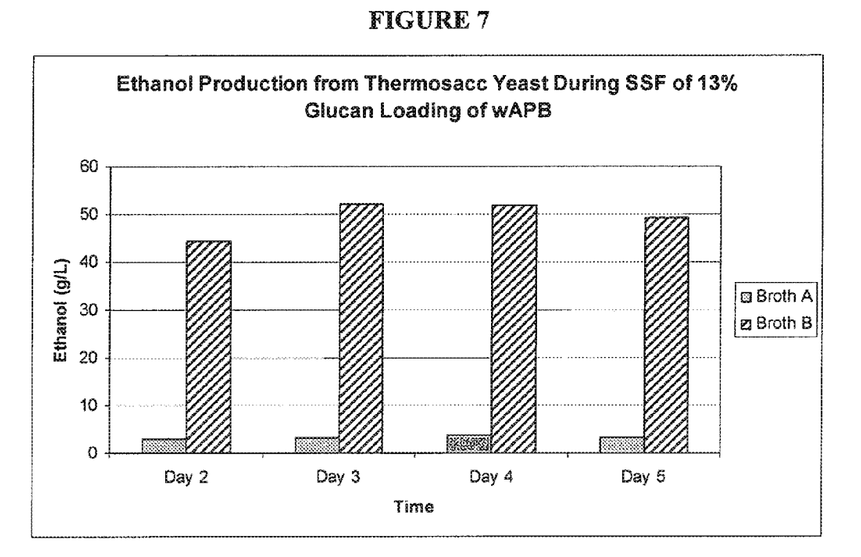
FIG. 7 shows ethanol production from Thermosacc yeast on washed APB hydrolysate as described in Example 2.
Figure 8:
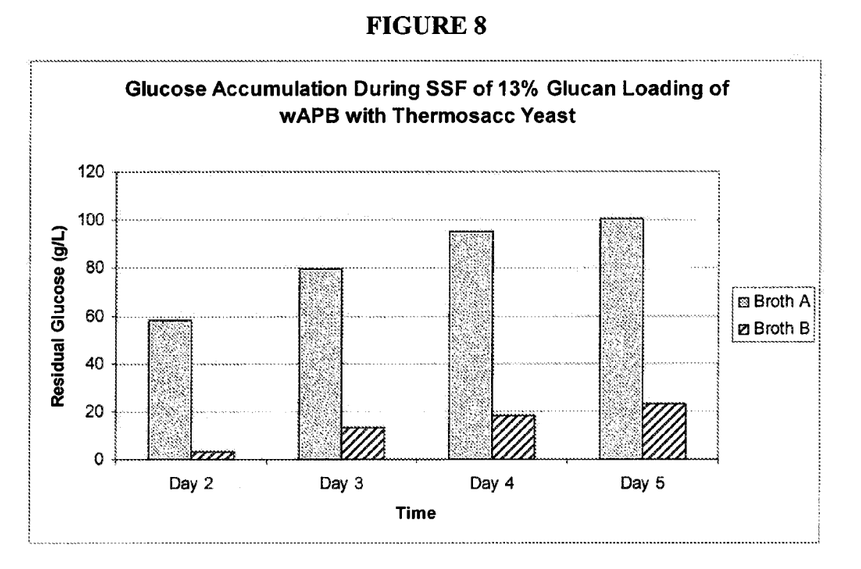
FIG. 8 shows glucose accumulation during Thermosacc yeast fermentation on washed APB hydrolysate as described in Example 2.

Washed acid pretreated bagasse, 50 mM sodium citrate buffer (pH 4.8), and Broth A or B were added to separate flasks at a concentration of 80 mg of protein per gram of substrate glucan. Each flask was then inoculated with 1% (v/w) of rehydrated Thermosacc yeast, and then inoculated with 1% (v/w) of yeast nutrients consisting of 10% (w/w) yeast extract, 10% (w/w) peptone, and 1% (w/w) glucose. Each flask was then incubated in a rotary shaker set to 38° C. and 150 rpm. The fermentation mixtures were sampled after 2, 3, 4, and 5 days of incubation and analyzed for ethanol and glucose concentrations following the procedure outlined below in the HPLC assay section. The results are shown in FIGS. 7 and 8.

HPLC Assay

All samples for HPLC analysis were diluted 10× in 5 mM sulfuric acid, and filtered through a 0.2 μm filter before injection into the HPLC. HPLC analysis was performed using a BioRad Aminex HPX-87H ion exclusion column (300 mm×7.8 mm).

Results

Broth A and B generated hydrolysate both produced over 130 g/L glucose, with percent glucose conversion of 90.4% and 92.6%, respectively. Lactic acid was not detected in either hydrolysate.

The concentration of lactic acid produced from *L. rhamnosus* increases with lower glucan loadings of wAPB suggesting a strong inhibitory effect from the substrate. At 13% glucan loading of wAPB Broth A and B generated hydrolysates the level of lactic acid produced was not significantly different from each other. Lactic acid production from *L. rhamnosus* on 7% glucan loading of wAPB generated from Broth A was 1.5 times greater than lactic acid production from Broth B generated hydrolysate. FIG. 6 is a graph comparing lactic acid production from *L. rhamnosus* on wAPB hydrolysate produced from Broths A and B.

Ethanol production from Thermosacc yeast on 13% glucan of wAPB hydrolysate generated from Broth A was 12.5 times greater than hydrolysate produced from Broth B (FIG. 7). FIG. 7 is a graph comparing ethanol production from Thermosacc yeast on 13% glucan wAPB hydrolysate generated from Broths A and B. After 5 days of Thermosacc yeast fermentation, residual glucose accumulation from Broth B generated hydrolysate was 4 times greater than Broth A generated hydrolysate. FIG. 8 is a graph comparing glucose accumulation during Thermosacc yeast fermentation of hydrolysate produced from Broths A and B.

Although the foregoing invention has been described in some detail by way of illustration and examples for purposes of clarity of understanding, it will be apparent to those skilled in the art that certain changes and modifications may be practiced without departing from the spirit and scope of the invention. Therefore, the description should not be construed as limiting the scope of the invention.

All publications, patents, and patent applications cited herein are hereby incorporated by reference in their entireties for all purposes and to the same extent as if each individual publication, patent, or patent application were specifically and individually indicated to be so incorporated by reference.

What is claimed is:

1. A method of making a fermentation broth formulation, comprising incubating a first mixture comprising:
   (a) one or more fermentation broths comprising microbial cells,
   (b) a first organic acid component comprising at least one 1-5 carbon organic acid and/or a salt thereof in an amount of from 0.1% to 15% by weight of said mixture, and
   (c) a second organic acid component comprising at least one 6 or more carbon organic acid and/or a salt thereof in an amount of from 0.025% to 5% by weight of said mixture,
   for a time period of 8 to 36 hours, and under conditions of at a temperature of 20° C. to 50° C., and a pH of 3.5 to 5, that result in at least a 4 log decrease in viable cells in said one or more fermentation broths, thereby making a fermentation broth formulation.

2. The method of claim 1, wherein said first organic acid component is in an amount of from 0.2% to 1%, from 0.2% to 0.5%, from 0.1% to 10%, from 0.25% to 5% or from 0.3% to 3% by weight of said first mixture.

3. The method of claim 1, wherein said second organic acid component is in an amount of from 0.04% to 3%, from 0.2% to 0.5%, from 0.1% to 1%, from 0.25% to 5% or from 0.3% to 3% by weight of said first mixture.

4. The method of claim 1 wherein said time period is from 20 hours to 28 hours.

5. The method of claim 1, wherein said temperature is 25° C. to 40° C.

6. The method of claim 5, wherein said temperature is 28° C. to 33° C.

7. The method of claim 1, wherein said pH is 4 to 4.7.

8. The method of claim 7, wherein said pH is 4.2 to 4.5.

9. The method of claim 1, wherein said incubating results in at least a 5 log decrease, a 6 log decrease, a 7 log decrease or an 8 log decrease in the number of viable cells in said one or more fermentation broths.

10. The method of claim 1, wherein said decrease in viable cells for the first mixture is at least 0.5-fold, at least 1-fold, at least 2-fold, at least 5-fold or at least 10-fold greater than for a second mixture subjected to said conditions, said second mixture containing only one of said first organic acid component and said second organic acid component, in an amount of up to the total weight percentages of the first and second organic acid components in said first mixture.

11. The method of claim 1, wherein said cells are fungal cells.

12. The method of claim 11, wherein the fungal cells are filamentous fungal cells.

13. The method of claim 12, wherein the filamentous fungal cells are from the genera *Trichoderma, Aspergillus, Penicillium, Humicola, Chrysosporium,* or *Neurospora.*

14. The method of claim 1, wherein the first organic acid component comprises or consists of acetic acid, a salt of acetic acid, formic acid, a salt of formic acid, propionic acid, a salt of propionic acid, or a mixture of two or more of the foregoing.

15. The method of claim 14, wherein the first organic acid component comprises or consists of acetic acid and/or a salt thereof.

16. The method of claim 1, wherein the second organic acid component comprises or consists of benzoic acid, a salt of benzoic acid, cyclohexanecarboxylic acid, a salt of cyclohexanecarboxylic acid, 4-methylvaleric acid, a salt of 4-methylvaleric acid, phenylacetic acid, a salt of phenylacetic acid, or a mixture of two or more of the foregoing.

17. The method of claim 16, wherein the second organic component comprises or consists of benzoic acid and/or a salt thereof.

18. The method of claim 1, wherein said first organic acid component comprises a sodium, potassium, calcium or magnesium salt of said 1-5 carbon organic acid and/or wherein said second organic acid component comprises a sodium, potassium, calcium or magnesium salt of said 6 or more carbon organic acid.

19. The method of claim 1, wherein said first organic acid component comprises acetic acid at a concentration of 0.2%-0.4% by weight and the second organic acid component comprises sodium benzoate at a concentration of 0.2%-0.4% by weight.

20. The method of claim 19, wherein said time period is 24 hours, said conditions are at a temperature of 40° C., and at a pH of between 4 and 4.6.

21. The method of claim 1, wherein at least one of said one or more fermentation broths contains one or more proteins secreted by said cells.

22. The method of claim 21, wherein said at least one of said one or more proteins is expressed recombinantly by said cells.

23. The method of claim 21, wherein at least one of said one or more proteins is an enzyme.

24. The method of claim 23, wherein said enzyme is an exoglucanase, an endoglucanase, a hemicellulase or a β-glucosidase.

25. The method of claim 21, wherein at least one of said one or more fermentation broths contains a plurality of enzymes expressed recombinantly and secreted by the cells.

26. The method of claim 25, wherein said plurality of enzymes is each an exoglucanase, an endoglucanase, a hemicellulase or a β-glucosidase.

27. The method of claim 1, wherein said conditions result in a fermentation broth formulation having at least 75%, at least 80%, at least 85%, at least 90%, at least 95% or at least 98% of enzymatic activity of said one or more fermentation broths.

28. The method of claim 1, wherein proteins constitute 5 to 15 weight percent of said first mixture.

29. The method of claim 1, further comprising the step of adding a pH-adjusting agent to said first mixture during said incubation period.

30. The method of claim 29, wherein said pH-adjusting agent is phosphoric acid.

31. The method of claim 29, wherein said pH-adjusting agent is sulfuric acid.

32. The method of claim 29, wherein said pH-adjusting agent is sodium hydroxide.

33. The method of claim 1, wherein said first mixture further comprises one or more anti-microbial agents.

34. The method of claim 33, wherein said one or more anti-microbial agents are in an amount of 0.0005 to 0.05 percent by weight of said first mixture.

35. The method of claim 34, wherein said one or more anti-microbial agents are in an amount of 0.001 to 0.025 percent by weight of said first mixture.

36. The method of claim 33, wherein the antimicrobial agent comprises hops extract containing iso-alpha-acids, tetra-iso alpha acids, and/or beta acids.

37. The method of claim 1, further comprising making said first mixture prior to said incubating step.

38. The method of claim 37, wherein said first mixture is made by a process comprising combining one or more fermentation broths with at least one 1-5 carbon organic acid and/or a salt thereof, at least one 6 or more carbon organic acid and/or a salt thereof and optionally one or more further reagents.

39. The method of claim 38, wherein said one or more further reagents comprise a pH adjusting agent and/or an anti-microbial agent.

40. A fermentation broth formulation obtained or obtainable by the method of claim 1.

41. The fermentation broth formulation of claim 40 which comprises one or more extracellular enzymes selected from an exoglucanase, an endoglucanase, a hemicellulase, and a β-glucosidase.

42. The fermentation broth formulation of claim 40 which has 2200 to 2800 CMC U/g of endoglucanase activity and 525 to 775 pNPG U/g of β-glucosidase activity.

43. The fermentation broth formulation of claim 40 which has 2200 to 3200 CMC U/g of endoglucanase activity, 300 to 800 pNPG U/g of β-glucosidase activity and 2000 to 5000 ABX U/g of xylanase activity.

44. A kit comprising (a) packaging; and (b) the fermentation broth formulation according to claim 40.

45. A composition comprising (a) one or more fermentation broths comprising microbial cells; (b) a first organic acid component comprising at least one 1-5carbon organic acid and/or a salt thereof in an amount of 0.2% to 1.5% by weight of said composition, (c) a second organic acid component comprising at least one 6 or more carbon organic acid and/or a salt thereof in an amount of 0.04% to 0.6% by weight of said composition, whereby the composition has a pH of 3.5 to 5.

46. A composition comprising (a) one or more fermentation broths comprising microbial cells; (b) a first organic acid component comprising at least one 1-5carbon organic acid and/or a salt thereof in an amount of from 0.2% to 1%, from 0.2% to 0.5%, from 0.1% to 10%, from 0.25% to 5% or from 0.3% to 3% by weight of said composition; and a second organic acid component comprising at least 6 or more carbon organic acid and/or a salt thereof in an amount of from 0.04% to 3%, from 0.2% to 0.5%, from 0.1% to 1%, from 0.25% to 5% or from 0.3% to 3% by weight of said composition, whereby the composition has a pH of 3.5to 5.

47. The composition of claim 46, wherein said cells are predominantly or completely nonviable cells.

48. The composition of claim 47, wherein if viable cells are present in said composition, then the ratio of nonviable cells to viable cells in said composition is at least 10:1, at least 50:1, at least 100:1, at least 1000:1, at least 10,000:1, at least 100,000:1 or at least 1,000,000:1.

49. The composition of claim 46, which has a pH of 4 to 4.7.

50. The composition of claim 49, which has a pH of 4.2 to 4.5.

51. The composition of claim 46, wherein said cells are fungal cells.

52. The composition of claim 51, wherein said fungal cells are filamentous fungal cells.

53. The composition of claim 52, wherein said filamentous fungal cells are from the genera *Trichoderma, Aspergillus, Penicillium, Humicola, Chrysosporium,* or *Neurospora*.

54. The composition of claim 46, wherein said first organic acid component comprises or consists of acetic acid, a salt of acetic acid, formic acid, a salt of formic acid, propionic acid, a salt of propionic acid, or a mixture of two or more of the foregoing.

55. The composition of claim 54, wherein said first organic acid component comprises or consists of acetic acid and/or a salt thereof.

56. The composition of claim 46, wherein said second organic acid component comprises or consists of benzoic acid, a salt of benzoic acid, cyclohexanecarboxylic acid, a salt of cyclohexanecarboxylic acid, 4-methylvaleric acid, a salt of 4-methylvaleric acid, phenylacetic acid, a salt of phenylacetic acid, or a mixture of two or more of the foregoing.

57. The composition of claim 56, wherein said second organic component comprises or consists of benzoic acid and/or a salt thereof.

58. The composition of claim 46, wherein said first organic acid component comprises a sodium, potassium, calcium or magnesium salt of said 1-5 carbon organic acid and/or wherein said second organic acid component comprises a sodium, potassium, calcium or magnesium salt of said 6 or more carbon organic acid.

59. The composition of claim 46, wherein said first organic acid component comprises acetic acid at a concentration of 0.2%-0.4% by weight and the second organic acid component comprises sodium benzoate at a concentration of 0.2%-0.4% by weight.

60. The composition of claim 46, which comprises one or more proteins secreted by said cells.

61. The composition of claim 60, wherein said at least one of said one or more proteins is expressed recombinantly by said cells.

62. The composition of claim 60, wherein at least one of said one or more proteins is an enzyme.

63. The composition of claim 62, wherein said enzyme is an exoglucanase, an endoglucanase, a hemicellulase or a β-glucosidase.

64. The composition of claim 46, which contains a plurality of enzymes that are expressed recombinantly and secreted by the cells.

65. The composition of claim 64, wherein said plurality of enzymes is each an exoglucanase, an endoglucanase, a hemicellulase or a β-glucosidase.

66. The composition of claim 46, wherein proteins constitute 5 to 15 weight percent of said composition.

67. The composition of claim 46, which further comprises one or more anti-microbial agents.

68. The composition of claim 67, wherein said one or more anti-microbial agents are in an amount of 0.0005 to 0.05 percent by weight of said composition.

69. The composition of claim 68, wherein said one or more anti-microbial agents are in an amount of 0.001 to 0.025 percent by weight of said composition.

70. The composition of claim 67, wherein the antimicrobial agent comprises hops extract containing iso-alpha-acids, tetra-iso alpha acids, and/or beta acids.

71. A kit comprising (a) packaging; and (b) the fermentation broth formulation according to claim 4.

* * * * *